(12) United States Patent
Beule et al.

(10) Patent No.: US 10,502,689 B2
(45) Date of Patent: Dec. 10, 2019

(54) PORTABLE READER MODULE, PORTABLE READER, AND METHOD FOR QUANTITATIVE ANALYSIS OF AN ASSAY

(71) Applicant: MicroDiscovery GmbH, Berlin (DE)

(72) Inventors: Dieter Beule, Berlin (DE); Johannes Schuchhardt, Berlin (DE); Arif Malik, Berlin (DE)

(73) Assignee: MicroDiscovery GmbH, Berlin (DE)

( * ) Notice: Subject to any disclaimer, the term of this patent is extended or adjusted under 35 U.S.C. 154(b) by 10 days.

(21) Appl. No.: 15/873,164

(22) Filed: Jan. 17, 2018

(65) Prior Publication Data
US 2018/0144468 A1    May 24, 2018

Related U.S. Application Data

(63) Continuation of application No. 14/222,219, filed on Mar. 21, 2014, now abandoned.

(30) Foreign Application Priority Data

Mar. 21, 2013   (EP) .................... 13160491

(51) Int. Cl.
*G01N 21/84*    (2006.01)
*G01N 33/50*    (2006.01)

(52) U.S. Cl.
CPC ..... *G01N 21/8483* (2013.01); *G01N 33/5017* (2013.01); *G06T 2207/10024* (2013.01); *G06T 2207/30004* (2013.01)

(58) Field of Classification Search
CPC ........... G01N 21/8483; G01N 33/5017; G06T 2207/10024; G06T 2207/30004
See application file for complete search history.

(56) References Cited

U.S. PATENT DOCUMENTS

| 5,408,535 A | 4/1995 | Howard, III et al. |
| 7,267,799 B1 | 9/2007 | Borich et al. |
| 7,803,322 B2 | 9/2010 | Borich et al. |
| 8,824,800 B2 | 9/2014 | Bremnes et al. |

(Continued)

FOREIGN PATENT DOCUMENTS

| EP | 2781910 | 9/2014 |
| WO | 2009/054729 | 4/2009 |

OTHER PUBLICATIONS

European Search Report dated Aug. 13, 2014 in EP 13160491.0 (5 pgs).

(Continued)

*Primary Examiner* — Samuel P Siefke
(74) *Attorney, Agent, or Firm* — Dicke, Billig & Czaja, PLLC

(57) ABSTRACT

A portable reader module includes a housing, a first receptacle configured to removably receive a portable device having an imager, and a second receptacle configured to removably receive a cartridge. The first receptacle includes a first optical entrance for the imager to the internal space of the housing. The second receptacle includes a second optical entrance to the internal space of the housing. A light-deflecting optical element is arranged within the internal space of the housing to define an optical path between the first optical entrance and the second optical entrance. An illuminating path for illuminating the cartridge is defined in the housing. The housing is configured to allow the internal space to be light-shielded.

18 Claims, 13 Drawing Sheets

(56) References Cited

U.S. PATENT DOCUMENTS

| | | |
|---|---|---|
| 8,889,424 B2 | 11/2014 | Ehrenkranz et al. |
| 8,916,390 B2 | 12/2014 | Ozcan et al. |
| 8,947,656 B2 | 2/2015 | Cunningham |
| 9,057,702 B2 | 6/2015 | Ozcan et al. |
| 2003/0112432 A1 | 6/2003 | Yguerabide et al. |
| 2003/0119202 A1 | 6/2003 | Kaylor et al. |
| 2005/0095697 A1 | 5/2005 | Bachur, Jr. et al. |
| 2006/0052709 A1 | 3/2006 | DeBaryshe et al. |
| 2006/0222567 A1 | 10/2006 | Kloepfer et al. |
| 2006/0292040 A1 | 12/2006 | Wickstead et al. |
| 2009/0236541 A1 | 9/2009 | Lomnes et al. |
| 2010/0315644 A1 | 12/2010 | Egan et al. |
| 2012/0063652 A1 | 3/2012 | Chen et al. |
| 2012/0282154 A1 | 11/2012 | Slowey et al. |
| 2013/0157351 A1 | 6/2013 | Ozcan et al. |
| 2013/0162981 A1 | 6/2013 | Emeric et al. |
| 2013/0184188 A1 | 7/2013 | Ewart et al. |
| 2013/0273524 A1 | 10/2013 | Ehrenkranz |
| 2013/0273528 A1 | 10/2013 | Ehrenkranz |
| 2014/0120563 A1 | 5/2014 | Ozcan et al. |
| 2014/0154789 A1 | 6/2014 | Polwart et al. |
| 2014/0186820 A1 | 7/2014 | Queval |
| 2014/0316732 A1 | 10/2014 | Dupoteau |
| 2014/0324373 A1 | 10/2014 | Xiang et al. |

OTHER PUBLICATIONS

European Search Report dated Aug. 12, 2015 in EP 15160358.6 (6 pgs).

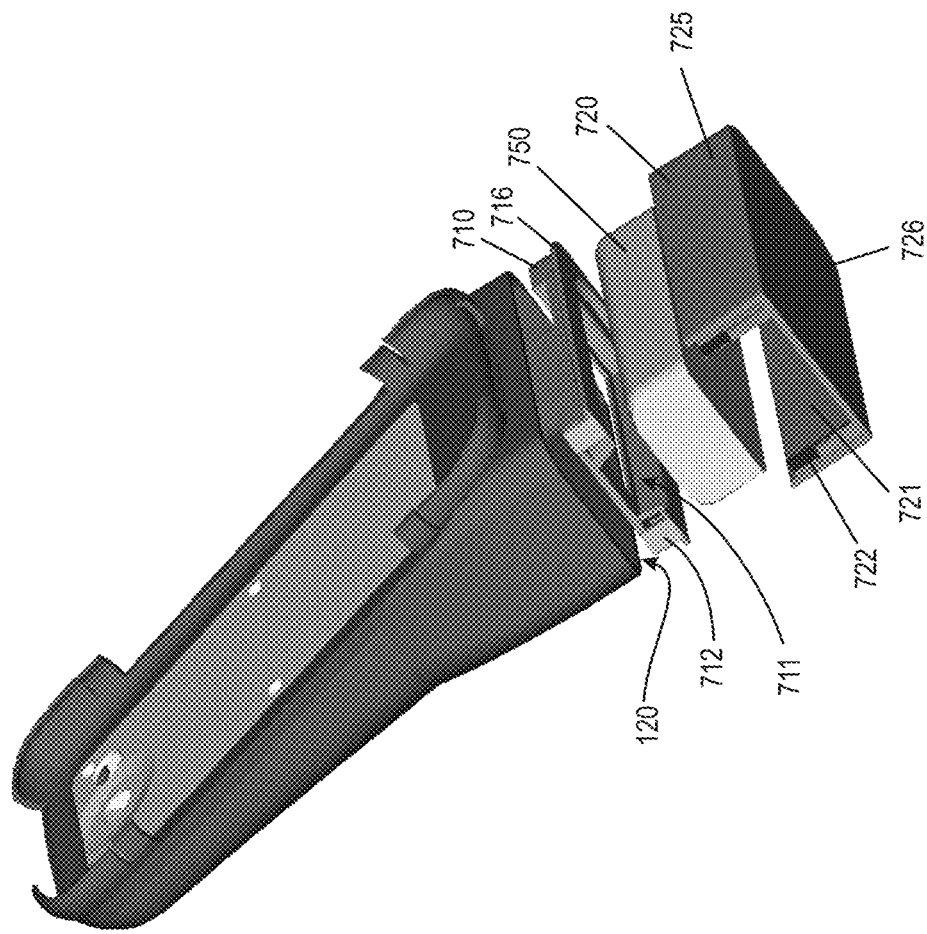
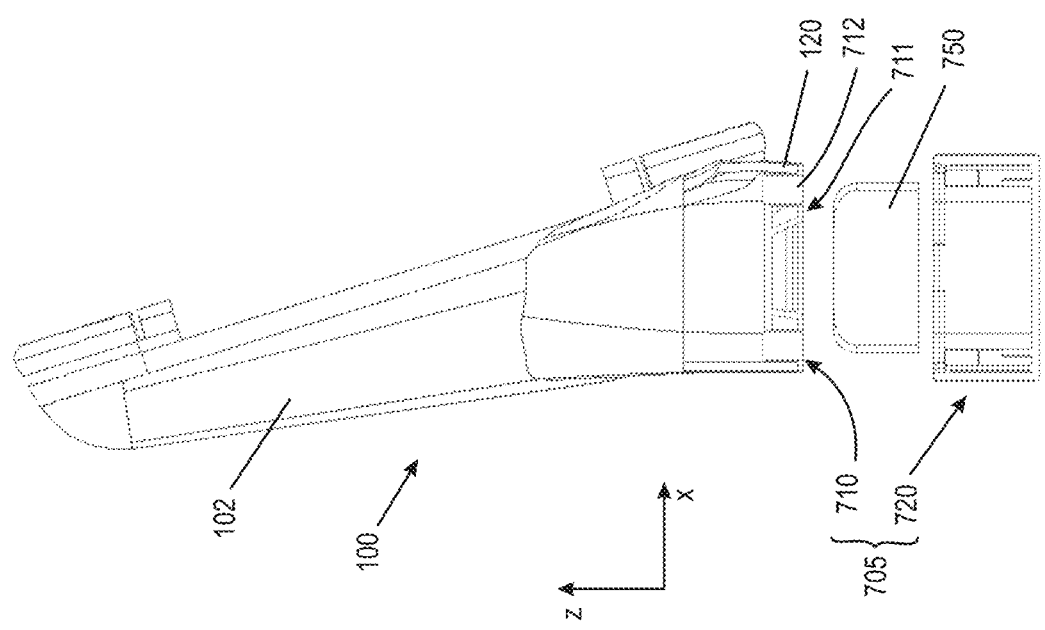

PORTABLE READER MODULE, PORTABLE READER, AND METHOD FOR QUANTITATIVE ANALYSIS OF AN ASSAY

CROSS-REFERENCE TO RELATED APPLICATIONS

This application is a continuation of U.S. application Ser. No. 14/222,219, filed Mar. 21, 2014, which claims priority to EP Patent Application No. 13160491.0, filed on Mar. 21, 2013, the entire teachings of which are incorporated herein by reference.

TECHNICAL FIELD

Embodiments described herein relate to a portable reader module and particularly to portable readers which can be used to quantitatively analyse images produced by a detection system, in particular assays such as immunoassays and chromatographic assays, for example lateral flow assays.

BACKGROUND

Immunoassays such as lateral flow rapid tests are widely used in in-vitro diagnostics, veterinary medicine and environmental analytic. These tests are based on an interaction of antibodies with antigens which brings about a change of a colour or colour or chromatic intensity or saturation of a test result region. The change of the colour or of the colour saturation can be assessed either with the naked eye or quantitatively. There are known stationary devices and portable devices for evaluating such tests.

For example, U.S. 2012/0063652A1 describes a smartphone-based method for evaluating colour-based reaction testing of biological materials by capturing a digital image of a test strip together with an adjacently-located reference colour chart in an uncontrolled environment.

U.S. Pat. No. 7,803,322 B2 describes a test media reader module.

WO 2009/054729 A1 describes an immunoassay analysis method.

The above described approaches, however, do not allow a reliable quantitative analysis of assays. In view of the above, there is need for improvement.

SUMMARY

According to an embodiment, a portable reader module includes a housing having an internal space, a first receptacle configured to removably receive a portable device having an imager, and a second receptacle configured to removably receive a cartridge. The first receptacle includes a first optical entrance for the imager to the internal space of the housing. The second receptacle includes a second optical entrance to the internal space of the housing so that the cartridge is visible to and from the internal space. A light-deflecting optical element is arranged within the internal space of the housing to define an optical path between the first optical entrance and the second optical entrance. An illuminating path for illuminating the cartridge is defined in the housing. The housing is configured to allow the internal space to be light-shielded.

According to an embodiment, a portable reader includes a portable reader module, and a portable device received in the first receptacle of the housing, wherein the portable device includes an imager, a central processing unit, and a display. The portable device is configured to capture an image of a cartridge including at least one test zone when the cartridge is received in the second receptacle of the housing, to process the captured image, and to display a test result.

According to an embodiment, a method for quantitative analysis of an assay includes providing a portable reader module; placing a portable device having an imager, a central processing unit, and a display unit in the first receptacle of the portable reader module; placing a cartridge having at least one test zone with at least one test result region in the second receptacle of the portable reader module; capturing an image of the cartridge including the test zone by the imager of the portable device using the illuminating path of the portable reader module to illuminate the cartridge; analysing the captured image by the portable device to obtain a test result; and displaying the test result in the display unit of the portable device.

Those skilled in the art will recognise additional features and advantages upon reading the following detailed description, and upon viewing the accompanying drawings.

BRIEF DESCRIPTION OF THE DRAWINGS

The components in the figures are not necessarily to scale, instead emphasis being placed upon illustrating the principles of the invention. Moreover, in the figures, like reference numerals designate corresponding parts. In the drawings:

FIGS. 16 and 17 illustrate a portable reader module having a cartridge adapter having a cartridge interface and a cartridge holder according to an embodiment;

DETAILED DESCRIPTION

Figure 1A:
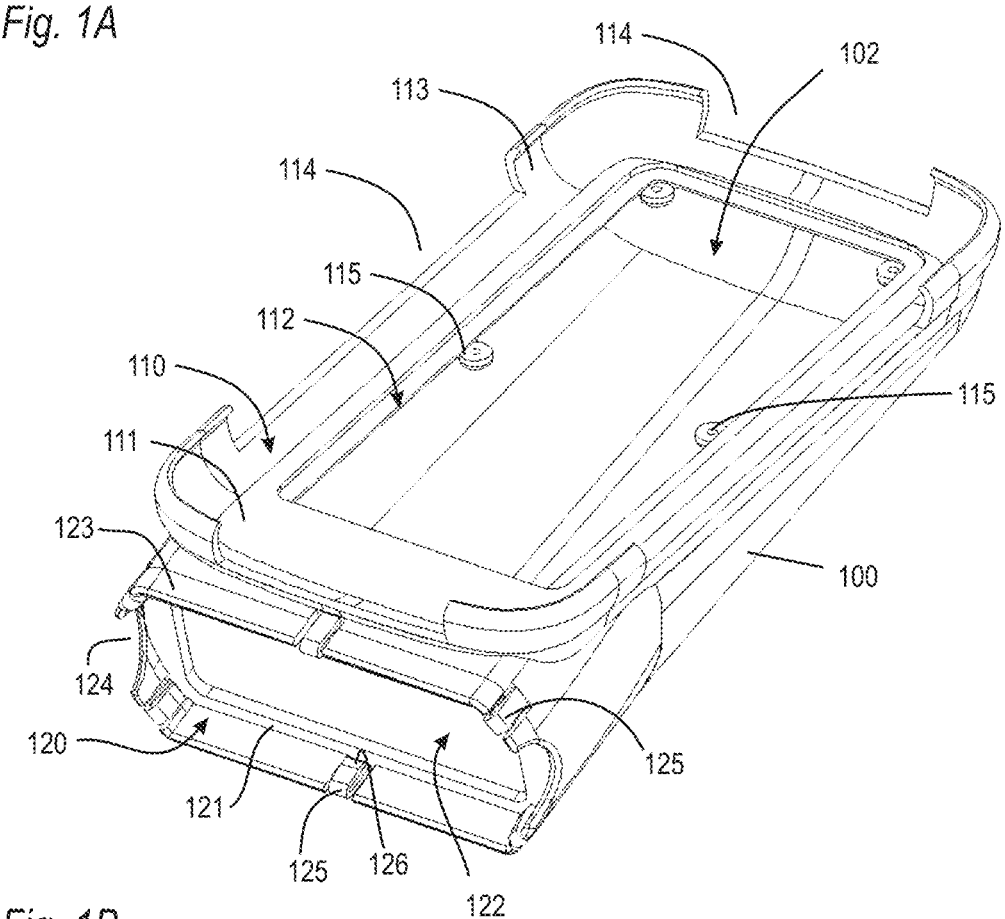
FIGS. 1A and 1B illustrate a portable reader module and a portable reader according to an embodiment.

In the following Detailed Description, reference is made to the accompanying drawings, which form a part hereof, and in which are shown by way of illustration specific embodiments in which the invention may be practised. In this regard, directional terminology, such as "top", "bottom", "front", "back", "leading", "trailing", "vertical", "lateral" etc., is used with reference to the orientation of the Figure(s) being described. Because components of embodiments can be positioned in a number of different orientations, the directional terminology is used for purpose of illustration and is in no way limiting. It is to be understood that other embodiments may be utilised and structural or logical changes may be made. The following detailed description, therefore, is not to be taken in a limiting sense, and the scope of the present invention is defined by the appended claims. The embodiments being described use specific language, which should not be construed as limiting the scope of the appended claims.

According to an embodiment, a portable reader module includes a housing which includes an internal space, a first receptacle configured to removably receive a portable device, and a second receptacle configured to removably receive a cartridge. The portable device includes an imager. The first receptacle includes a first optical entrance for the imager to the internal space of the housing, and the second receptacle includes a second optical entrance to the internal space of the housing so that the cartridge is visible to the internal space. A light-deflecting optical element is arranged within the internal space of the housing to define an optical path between the first optical entrance and the second optical entrance. An illuminating path for illuminating the cartridge is defined in the housing, wherein the housing is configured to allow the internal space to be light-shielded.

The housing forms a light-shielded environment to provide a light-controlled environment for image acquisition. For example, the housing is configured to sufficiently block or reduce interfering ambient light. This is beneficial for the quantitative analysis of the assays as ambient light can change and its influence on quantitative evaluation is difficult to control.

The housing includes two receptacles, one for the mobile device and one for the cartridge. Each of the receptacles includes or forms a respective optical entrance to the internal space of the housing. Typically, the receptacles are configured such that the optical entrances are covered when the mobile device and the cartridge are placed into the respective receptacles. Light-tightness can be increased by suitable sealings or suitable shape of the receptacles so that no ambient light can enter the internal space.

The optical entrances can be formed or closed by transparent materials such a glass or transparent plastic windows to prevent dust or other foreign particles to enter the internal space. The windows can be releasably mounted to allow exchange of broken or damaged windows.

According to an embodiment, the windows are provided with a coating such as optical filters and/or have structured surfaces to reduce or avoid reflexions. The window can also be slightly tilted against the optical axis to remove specular reflections.

Typically, except for the two optical entrances, the housing does not provide any further opening to maintain the light-blocking capability. Hence, the housing is typically closed. When the housing is provided with additional openings, for example to allow access to a light source or for adjusting or changing the optical element, covers can be provided which cover those openings during use.

The light-deflecting optical element arranged in the housing allows the imager of the mobile device, when placed in the first receptacle, to capture an image of the cartridge. To this end, the light-deflecting optical element provides a specular deflection such as a reflexion by a mirror or a deflection by a prism. The optical path defined by the optical element is bent or flexed within the housing allowing the housing to be provided with a compact size while ensuring a sufficiently long optical distance between the imager and the cartridge. This is beneficial for the optical imaging. Unlike other approaches, which need to place the mobile device at a given distance from the cartridge or which need extra refraction optics, the mobile device can be placed in close geometrical proximity to the cartridge while maintaining a sufficiently long optical distance.

Typically, the optical path is bent or reflected at least one time. In addition to increasing the optical distance, bending of the optical path by the light-deflecting optical element also provides more freedom for the relative orientation of the portable device to the cartridge. For example, the mobile device can be kept in a substantially upright position while the cartridge remains in a horizontal orientation. The housing can thus be provided with a compact and user-friendly size. For example, according to an embodiment, the second receptacle is configured to be placeable, with our without an inserted cartridge, onto a horizontal surface so that a portable device, when received in the first receptacle, is in a substantially upright position relative to the surface. The portable reader can thus be placed, for example, on a table after inserting the cartridge, with the mobile device being held in an upright position to facilitate user interaction and ergonomic handling. Furthermore, the housing can have an external shape suitable for gripping with one hand while the other hand of the user is free for, for example, inserting a cartridge or operating the portable device.

For the purpose of this specification, "substantially upright position" means a vertical position and also an inclined position, which can be, for example inclined with respect to a vertical orientation up to about 10°, in some embodiments up to about 20°. A slight inclination is beneficial as it ensure that the centre of gravity of the mobile device is above the second receptacle on which the housing stands so that upright position is stable.

For further improvement of the optical imaging, the housing includes, according to an embodiment, an adjustment element configured to adjust the location and/or orientation of the optical element. Any misalignment between the mobile device, particularly the imager of the mobile device, and the cartridge can be eliminated or reduced by the adjustment element.

The illuminating path defined within the housing for illuminating the cartridge can be separate to the optical path for capturing images to prevent direct light exposure of the imager.

According to an embodiment, the portable device includes a light source. The illuminating path can include a reflector or any other suitable reflecting means for reflecting light from the light source to the cartridge. The reflector can provide a specular reflexion or a diffuse reflexion. For example, a portion of the internal walls of the housing can be provided with light-reflecting surface properties to evenly distribute the light emitted from the mobile device's light source. Alternatively, a separate reflector such as a mirror or a diffuse reflector can be arranged in proximity to the optical entrance through which the light from the light source enters the internal space. When using the mobile device's light source, no extra light sources and extra voltage supplies are needed. Furthermore, the intensity of the light source of the mobile device can be directly controlled during capturing of the images so that optimal light conditions can be provided.

According to an embodiment, the illuminating path includes a light source arranged within the internal space of the housing. In addition to or alternatively to the light source of the mobile device, an extra light source can be used which provides more freedom in tailoring the light conditions. For example, a light source arranged in the housing can emit light of a different wavelength than the light source of the mobile device. Alternatively, when the portable device is not provided with a light source, the light source arranged in the housing ensures optimal light conditions. The light source can be arranged between the cartridge and the mobile device. Typically, the light source is arranged such that it illuminates the side of the cartridge which faces the light-deflecting optical element to illuminate the cartridge in light-reflected mode different to a light-transmitting illumination. The light source and the imager can be arranged to face the same side of the cartridge.

The light source arranged in the housing can be driven by a separate power supply or by the power supply of the mobile device, such as its battery.

According to an embodiment, the first and/or the second receptacle include holders for retaining the portable device in the first receptacle and/or the cartridge in the second receptacle. The respective holders ensure that the mobile device and the cartridge securely remain in place during use. The portable reader therefore does not need to be operated in a stationary environment during measurement but can be kept in hand. The holders, together with the receptacles, furthermore keep the mobile device and the cartridge in a given position relative to each other. For example, the holders can be elastic brackets snapping behind the mobile device and the cartridges for proper positioning. Basically, the holders can be of any type as long as they allow to maintain the portable device and/or the cartridge to securely remain in place. "Securely remain in place" means that the typical forces and accelerations generated during normal use are not sufficient to remove the mobile device and/or the cartridge from their respective receptacles.

Examples for holders are snap-in brackets, for example made integral with the material of the housing or mould onto the housing, or formed of a material different to the material of the housing. Examples are metallic clamping springs. Other examples are clamping springs with arrestor, fasting collars, flexible, for example, circumferential lips, and combination of the above described examples.

According to an embodiment, the receptacles are formed to allow lateral sliding or pushing-in of the portable device and/or the cartridge into the respective receptacle. This is particularly useful for the cartridge as in this case the second receptacle can be formed as a closed housing defining a bottom surface on which the housing can stand to keep the mobile device in a substantially upright position. For example, the second receptacle can have a slit at one of its sides through which the cartridge is inserted.

According to an embodiment, the housing can stand on the holders of the second receptacle, for example on edges of brackets used to hold the cartridge in the second receptacle.

According to an embodiment, the first receptacle includes a bottom element which is removably attached to the housing and which includes a holder to hold the light-deflecting optical element in the internal space. The holder for the light-deflecting optical element is thus attached to the bottom element of the receptacle and therefore aligned with the receptacle. When removing the bottom element, an access to the internal space of the housing can be provided, for example to exchange parts or to clean the internal space. Furthermore, the bottom element can be replaced or exchanged with a bottom element for another type of mobile devices.

The housing is made of non-transparent material such as plastic, for example black plastic material. The inner surface portions of the housing, which define the internal space, can be provided with a low-reflexion surface, for example, can have a corrugated surface.

To facilitate removal of a cartridge which is inserted into the second receptacle, the second receptacle can include recesses or cavities in lateral walls which allow gripping of the cartridge. This is also beneficial for inserting the cartridge. For example, the recesses can be formed between adjacent brackets for holding the cartridge.

According to an embodiment, at least portions of the internal space are provided with a low-reflexion surface to minimise unwanted reflexion. For example, the internal walls of the housing in proximity to the cartridge can be provided with a low-reflexion surface while the internal walls of the housing in proximity to the light source of the mobile device can be provided with a diffuse reflecting surface to improve light distribution.

The mobile device can be a smartphone, a mobile phone, a PDA (personal digital assistant), a tablet, or another mobile device which includes an imager suitable to capture photos. In addition to the imager, the mobile device typically includes a CPU and a display. The mobile device can also include other components such as a light source, which is, when used as illumination source for the imager, placed closed to the imager. The mobile device can furthermore include at least one wireless interface allowing the mobile device to connect to a network such as a WLAN and a mobile phone network.

The cartridge typically includes at least one test zone with at least one test result region responsive to a change of ambient conditions such as the presence of chemical or biological species. For example, the test result region can be responsive to the presence of analytes such as drug metabolites, hormones, germs such as anthrax, pH, lactate, and blood glucose. According to an embodiment, the cartridge includes at least two test result regions for simultaneously detecting and analysing two different analytes. In a specific embodiment, a plurality of test result regions is provided by the cartridge to allow simultaneous detection and analysis of a number of different analytes.

According to an embodiment, the cartridge can be a carrier adapted to carry one or more separate test strips or other separate test plates. The test strips or test plates can be removably attached to the cartridge. Typically, the cartridge is configured to keep the test strip or test plate in a predefined location and with a predefined orientation relative to the cartridge so that, when the cartridge bearing the test strip is inserted into the second receptacle, the test strip is aligned with the housing. Cartridges adapted for removably holding test strips or test plates are also referred to as carrier cartridges.

A cartridge can be a carrier adapted to hold any kind of image generating detection system supporting automated analysis like e.g. a plate holding a histological sample, or an array of possibly different samples or an electrophoretic device like a 2D gel, A cartridge can be designed to present the results of a multi-parallel sequencing process for further analysis.

The cartridge can include a housing with an opening to expose the test zone so that the test zone is visible. The housing accommodates a test medium which forms the test zone.

Cartridges can be of different shape and size. To accommodate different cartridges, adapters are provided according to an embodiment. The adapters are configured to be insertable into the second receptacle while allowing holding the cartridge so that the cartridge remains exposed or visible to the internal space.

Typically, the cartridges are made of an optically non-transparent material. For optically transparent or semi-transparent cartridges, the second receptacle can be provided with a cap or cover which can be slipped over the second receptacle including the inserted cartridge. According to an embodiment, the cap or cover is movably connected to the housing, for example by an articulation, so that the cap is movable between a close position to close the second receptacle and an open position allowing the cartridge to be inserted into and removed from the second receptacle. Also in this case, the housing together with the cap ensures a light-controlled environment.

To prevent that a cartridge is incorrectly inserted, the second receptacle can be provided with keying means which ensure that the cartridge can only be inserted with the correct orientation.

The portable reader module thus allows using a mobile device for the detection and analysis of the assays provided by a cartridge. The portable reader module provides the means for mounting and adjusting the mobile device forming a detection device relative to a cartridge to be tested in a specific orientation at a defined distance. Together with the mobile device, the portable reader module forms a portable reader which allows quantitatively analysis of the one or more test result regions of the cartridge after inserting a cartridge into the second receptacle.

Hence, the portable reader enables the quantitative detection of single or multiplexed probes interacting to markers either attached to a solid surface or being in solution. The probes might be amplified in the cartridge before detection e.g. with PCR or similar methods. The interacting molecules are labelled e.g. with chemical, enzymatic, colorimetric processes or with the interaction of probes having natural or synthetically attached coloured properties.

According to an embodiment, the portable reader module further includes an adapter for holding the cartridge. Using an adapter allows adaptation of the portable reader module on cartridges having different size and shape. The adapter can form a part of the housing and then defines, together with the second receptacle, an accommodation adapted for a specific type of cartridge.

According to an embodiment, the adapter for holding the cartridge includes a cartridge interface which is inserted into and accommodated by the second receptacle, and a cartridge holder for holding the cartridge. The cartridge holder cooperates with the cartridge interface when the cartridge holder is releasably attached to the cartridge interface. The cartridge interface typically remains inserted in the second receptacle and allows easy attachment of the cartridge holder which holds the cartridge.

According to an embodiment, one of the cartridge holder and cartridge interface includes magnetic bodies and the other one of the cartridge holder and the cartridge interface includes metal pins which cooperate together with the magnetic bodies to hold the cartridge holder in place relative to the cartridge interface. The magnetic bodies and the metallic pins together form a magnetic holding arrangement.

According to an embodiment, the cartridge interface includes the magnetic bodies and the cartridge holder includes metal pins or discs of a ferromagnetic metal or metal alloy. Ferromagnetic metals and metal alloys include at least one of iron, nickel and cobalt. The cartridge holder can be a disposable part, for example for easy handling of the cartridge which is disposed after use.

The cartridge interface can be designed to enable attachment of different types of cartridge holders. For example, the cartridge interface includes the magnetic bodies at predefined locations while the different types of cartridge holder have the pins or discs at corresponding locations. The cartridge holders can be designed for holding different types of cartridges. The different types of cartridges can differ from each other in size and shape so that the respective cartridge holder needs to be adapted to the given geometry of the cartridge.

According to an embodiment, the cartridge is pressed by the cartridge holder against the cartridge interface when the cartridge holder is attached to the cartridge interface.

According to an embodiment, the cartridge interface has a central opening which can be covered by a transparent window. The cartridge is placed below the transparent window to be visible from the internal space of the housing.

According to an embodiment, at least one of the cartridge holder and the cartridge interface includes keying elements for aligning the cartridge holder relative to the cartridge interface. In addition to that, the cartridge holder can include keying elements to align the cartridge within the cartridge holder relative to the cartridge holder. The cartridge is therefore aligned relative to the second receptacle and the mobile device.

Alignment between the cartridge holder and the housing can be mediated either through the cartridge interface or through a cooperation of the cartridge interface and the housing. For example, a lateral alignment can be brought about by engagement of the cartridge holder with the housing while a vertical alignment, i.e. in a direction along which the cartridge holder is placed onto the cartridge interface, is brought about by cooperation between the cartridge holder and the cartridge interface.

For ensuring light-tightness, the cartridge holder can enclose the outer periphery of the lower end of the housing. This engagement can also effect the lateral alignment.

The cartridge interface can include a large opening defining the second optical entrance.

According to an embodiment, the portable reader module further includes at least a first optical reference element configured to allow calibration and/or self-testing of the portable device, wherein the first optical reference element is arranged in the housing separate to the cartridge.

According to an embodiment, the portable reader module further includes at least a first optical reference element configured to allow calibration and/or self-testing of the portable device, wherein the first optical reference element is arranged inside of the second receptacle.

According to an embodiment, the portable reader module further includes a second optical reference element configured to allow calibration and/or self-testing of the portable device, wherein the second optical reference element differs from the first optical reference element in at least one of pattern, greyscale, and colour.

The portable reader module can include a first optical reference element or a first optical reference element and a second optical reference element which is different to the first optical reference. These optical reference elements are arranged, according to an embodiment, in the housing, typically in close proximity to the optical entrance of the second receptacle. For example, a transparent window closing the optical entrance of the second receptacle may be provided with optical references. In addition to that or alternatively, a separate film including the optical references can be placed on an internal side of the window. Furthermore, optical references can be formed on internal walls such as internal shoulders forming flat surface portions which are substantially perpendicular to the optical path.

The optical reference elements can be arranged on opposite sides of the test zone to facilitate the positional identification of the test zone. For example, once the optical reference elements have been identified, the used algorithm can restrict the field of search for the test zone to a region lying between the optical reference elements. In an embodiment, optical reference elements are arranged at four corners around the test zone or around the test zone.

One or more of the optical reference elements can also be provided by a special test cartridge which is inserted into the second receptacle and used to calibrate the portable reader.

The added optical reference elements can be, for example, patterns, which in combination with suitable software algorithms allow signal detection, quantification, classification, system self-test, calibration and user interaction with the portable device.

For example, using two or even three different types of optical reference elements significantly improve the reliability of the detection of the test zone including the test result region, the colorimetric correct detection of the colour change of the test result region, and the quantitative evaluation of the thus obtained test results and their correlation to, for example, other analytes. The optical reference elements also allow a self-test of the portable reader even when no cartridge is inserted. Such self-tests and self-calibrations are beneficial for verifying the quantitative evaluation.

Therefore, the mobile reader is equipped with means allowing automatic quantitative processing of calibration references (optical reference elements) and software algorithms for reliable signal quantification and user interaction.

When in use, the portable reader can first run a self-test and/or a self-calibration using the optical reference elements provided in the housing. These tests can be run independently of an inserted cartridge so that the portable reader can be brought into a calibrated state before the first use. Self-testing also ensure that changes of illuminating conditions, for example due to malfunctioned optical light sources, can be detected.

The optical reference element or elements includes suitable markers and references for algorithm-based determination of quantification area and quantification references. The optical reference elements can contain positional reference like crosses, lines, checker boards and other patterns, intensity references grey scales or grey step wedges, colour references like colour scales or colour step wedges.

According to an embodiment, the portable reader module further includes one or more identification marks uniquely identifying at least one individual component or part of the portable reader module. A component or part can refer to, for example, the housing, the cartridge interface or a reference element. The identification mark can be, for example, arranged within the housing at a location within the inspection range of the imager of the mobile device so that it can be optically recognized. The mobile device, automatically or upon a user request, recognizes the identification mark and uses the identification mark to obtain information specific to the component or part. The information is then used for adapting the calibration workflow or for the calibration procedure.

The algorithm for determination of the quantification area can include any combination of the following processes: (a) coarse cutting of the captured camera image which includes images of the optical reference elements, (b) finding the positional optical reference contained in the optical reference, (c) determination of search areas for the test result region (which can be, for example, strips), (e) detection of the strip positions and determination of their quantification area (e.g. width) within each search region either independent for each strip or multiple strips at a time, (f) reliable positioning quantification area of no signal/weak strips with respect to strips with clear signal.

According to an embodiment, the portable reader is capable of analysing not only single strips, which are typically used in lateral flow assays, but also of multiple test result regions such as a plurality of spots which are responsive to different analytes. The analysis of more than one test result region is enabled by the portable reader's capabilities for self-testing and self-calibration, and also by dedicated software algorithm for multiple-spot analysis which are presently only available for large test equipment.

According to an embodiment, a method for quantitative analysis of an assay includes providing a portable reader module; placing a portable device having an imager, a central processing unit, and a display unit in the first receptacle of the portable reader module; placing a cartridge including at least one test zone with at least one test result region in the second receptacle of the portable reader module; capturing an image of the cartridge including the test zone by the imager of the portable device using a light source to illuminate the cartridge; analysing the captured image by the portable device to obtain a test result; and displaying the test result in the display unit of the portable device. The test result can be, for example, a quantity of an analyte, such as an absolute or relative quantification value or a derived quantity as a ratio thereof, for which the test zone is specific, or can be merely a decision that a test is positive or negative. The method for quantitative analysis can include a calibration procedure and a quantitative evaluation procedure, or only a quantitative evaluation procedure, if the calibration has been done previously.

According to an embodiment, the method further includes capturing an image of the first optical reference element and/or the second optical reference element; identifying the first optical reference element in the captured image to obtain a positional calibration component; and using the obtained positional calibration component to locate the test zone and/or the test result region in the test zone.

According to an embodiment, the method further includes identifying the second optical reference element in the captured image to obtain a colorimetric calibration component; and using the obtained colorimetric calibration component to evaluate the colour and/or the chroma of the test result region in the test zone.

According to an embodiment, wherein the image of the cartridge and the image of the first and/or second optical reference are taken simultaneously.

According to an embodiment, the method includes displaying the image, or a portion of the captured image with regions identified as regions of interests such as the test zone and regions where the optical reference elements are arranged, and requesting a user-confirmation that the detection of these regions are correct. This semi-automatic approach allows the user to verify that the location of the test zone and other regions has been correctly carried out which prevents that quantitative analysis is carried out on incorrect regions. The user is prompted to confirm the correct local identification. After the confirmation, the method proceeds to the quantitative evaluation.

According to an embodiment, the method includes prompting the user's confirmation for final detection of the test result regions. To this end, the image can be displayed with marked test result regions, for example the highlighted strip region, for example by placing a rectangular around each test strip region or spot region. Hence, the method can include two processes which ask for user confirmation. This allows for optical verification of the procedures by the user.

According to an embodiment, after quantitative analysis, the user is prompted to accept or decline the result.

According to an embodiment, the procedures carried out and the user's confirmations can be logged in a log file to allow later verification of the analysis process and the results.

According to an embodiment, the cartridge is provided with additional optical reference elements such as bar codes or crosses. These additional optical reference elements can be used, in connection with the optical reference elements arranged in the housing, for verification of the localisation procedures. Furthermore, the additional optical reference elements can also be used to detect whether are cartridge has been correctly inserted. Moreover, the additional optical reference elements can include coded information, for example about the nature of the test provided by the cartridge. The coded information can be read and decoded by the mobile device and used for positional and quantitative evaluation.

According to an embodiment, a method for quantitative analysis of an assay includes providing a portable reader module comprising a housing, the housing including an internal space, a first receptacle for removably receiving a portable device, a second receptacle for removably receiving a cartridge, and at least a first optical reference element in the internal space of the housing; placing a portable device comprising an imager, a central processing unit, and a display unit in the first receptacle of the portable reader module; placing a cartridge including at least one test zone with at least one test result region in the second receptacle of the portable reader module; capturing an image of the cartridge including the test zone and the first optical reference by the imager of the portable device; identifying the first optical reference element in the captured image to obtain a positional calibration component; and using the obtained positional calibration component to locate the test zone and/or the test result region in the test zone.

According to an embodiment, the portable reader module further comprises a second optical reference element different to the first optical reference element in at least one of pattern, greyscale, and colour, wherein the second optical reference is captured together with the first optical reference element and the cartridge. The method further includes identifying the second optical reference element in the captured image to obtain a colorimetric calibration component; and using the obtained colorimetric calibration component to evaluate the colour and/or the colour saturation and/or the chroma of the test result region in the test zone.

The optical reference elements are typically arranged spaced to the test zone of the cartridge at the periphery of the second optical entrance. This enhances the system's capabilities to localise the test zone as test zone is surrounded by the optical reference elements.

In addition to that, pre-saved information in the mobile device on the geometrical structure of the test result region or regions, such as whether the test result regions have the shape of stripes or of spots and which colour they have, can be used to enhance the localisation of the test zone. Furthermore, pre-saved algorithms can be selected based on coded information provided by the cartridge such as bar codes printed on the cartridge. In addition to that or alternatively, the algorithms can be parameterised based the pre-saved or coded information.

According to an embodiment, the method includes identifying the second optical reference element in the captured image to obtain a colorimetric calibration component; and using the obtained colorimetric calibration component to evaluate the colour and/or the chroma of the test result region in the test zone thus allowing parallel monitoring and quantification of several calibrated colour channels.

According to an embodiment, a portable reader includes a portable reader module; a portable device received in the first receptacle of the housing, the portable device comprising an imager, a central processing unit, a display, and a light source; and a cartridge including at least one test zone received in the second receptacle of the housing, wherein the portable device is configured to capture an image including the test zone of the cartridge, to process the captured image, and to display a test result.

According to an embodiment, the method further includes capturing, by the imager of the portable device, an image of at least one identification mark which uniquely identifies at least one individual part of the reader module; processing the captured image of the identification mark to obtain an identifier; establishing a connection to a database to obtain information specific to the individual part of the reader module using the obtained identifier as a database key; and adapting a workflow of at least one of a calibration procedure and a quantitative evaluation procedure depending on the obtained information from the database.

The recognition of the identification mark by the mobile device, and the information obtained from the database, can be used to adapt the workflow for the calibration or the quantitative evaluation procedure. This can be done either automatically or in connection with user interaction, for example, when a test or reference cartridge needs to be inserted into the second receptacle or the adapter. For example, when the identification mark identifies the specific cartridge interface which is fixed in the second receptacle, the mobile device is capable of identifying whether it has already carried out a calibration together with this particular cartridge interface. As the cartridge interfaces can vary due to manufacturing tolerances, for each cartridge interface a separate calibration can be performed to take account of the tolerance. The same applies to, for example, the housings which can also vary due to manufacturing tolerances. For example, the angle of deflection defined by the holder for the light-deflecting optical element may vary among different housings and thus a respective calibration is performed.

Depending on the information obtained from the database, the workflow for the calibration and the quantitative evaluation is adapted. For example, when the mobile device recognizes that it had already conducted a calibration for this particular housing and/or cartridge interface, no additional calibration is needed or only a calibration verification is conducted. The obtained information then includes calibration parameters which are used by the mobile device's software to parameterize the quantitative evaluation procedure for analysis the tests. If no calibration was previously performed, a calibration is initiated by the mobile device's software.

An embodiment is described next with reference to FIGS. 1A and 1B. FIG. 1A shows a portable reader module having a housing 100 forming an internal space 102. A first receptacle 110 is formed by wall portions of the housing and has the shape of a half-shell with a large outer opening through which a portable device can be pushed into the first receptacle 110.

The first receptacle 110 includes a bottom wall portion 111 formed integral with the housing 100. The bottom wall portion 111 includes a large opening 112 which allows access to the internal space 102 of the housing 100. The large opening 112 is shown to assume nearly the complete area of the bottom wall portion 111. The actual size of the opening 112 can be, however, smaller than shown in FIG. 1A. Along the outer periphery of the bottom wall portion 111, lateral wall portions 113 are formed integral with the housing 100. The lateral wall portions 113 are convex in shape, and the inner surface of the lateral wall portions 113 are adapted to correspond to the lateral outer shape of the mobile device. Although the present embodiments are not restricted to a particular mobile device, the first receptacle 110 including its bottom wall portion 111 and lateral wall portions 113 is adapted to correspond to the outer shape of a specific mobile device since suitable mobile devices differ in their outer shape and size.

The lateral wall portions 113 are particularly formed where the corners of the mobile device will rest. This is best shown in FIG. 1B showing the portable reader module with inserted mobile device 300. The mobile device 300 is pushed with its backside ahead into the first receptacle 110 so that each of the four corners of the mobile device 300 is laterally surrounded by respective lateral wall portions 113. As shown in FIGS. 1A and 1B, the lateral wall portions 113 partially engages behind the front surface of the mobile device 300 to grab the mobile device and to keep it in place. To keep the mobile device 300 securely in place, the lateral wall portions 113 define by their upper ends, or free ends, an entry opening which is slightly smaller than the maximum lateral size of the mobile device. When pushing the mobile device 300 into the first receptacle 110, the lateral wall portions 113 are slightly laterally deflected and snap back to their original position when the maximal outer cross-section of the mobile device passes the upper ends of the lateral wall portions 113. To facilitates pushing in, and also removing, of the portable device 300, the wall thickness of the lateral wall portions 113 are adapted to provide the lateral wall portions 113 with a given flexibility. The lateral wall portions 113 therefore form elastic holders for holding the mobile device in the first receptacle 110.

To facilitate insertion and also taking out of the mobile device, recesses 114 are formed between adjacent lateral wall portions 113 to allow grabbing of the mobile device 300 and to allow access to connectors and/or switches which are often arranged on the lateral rim of the mobile device 300. The recesses 114 also allow that the lateral side walls 113 can deflect when the mobile device 300 is pushed into the first receptacle 110.

The housing 100 furthermore includes structures to allow a bottom element which closes the large opening 112 to be removably attached with the housing 100. These structures are projections 115 in this particular embodiment which are formed integral with the housing 100 and which include a female thread for a screw to be inserted. The bottom element, for example shown in FIGS. 3, 4A and 4B, rests onto the projections 115 when inserted to flush with the bottom wall portion 111. The first receptacle 110 is then provided with a flat bottom.

Figure 1B:
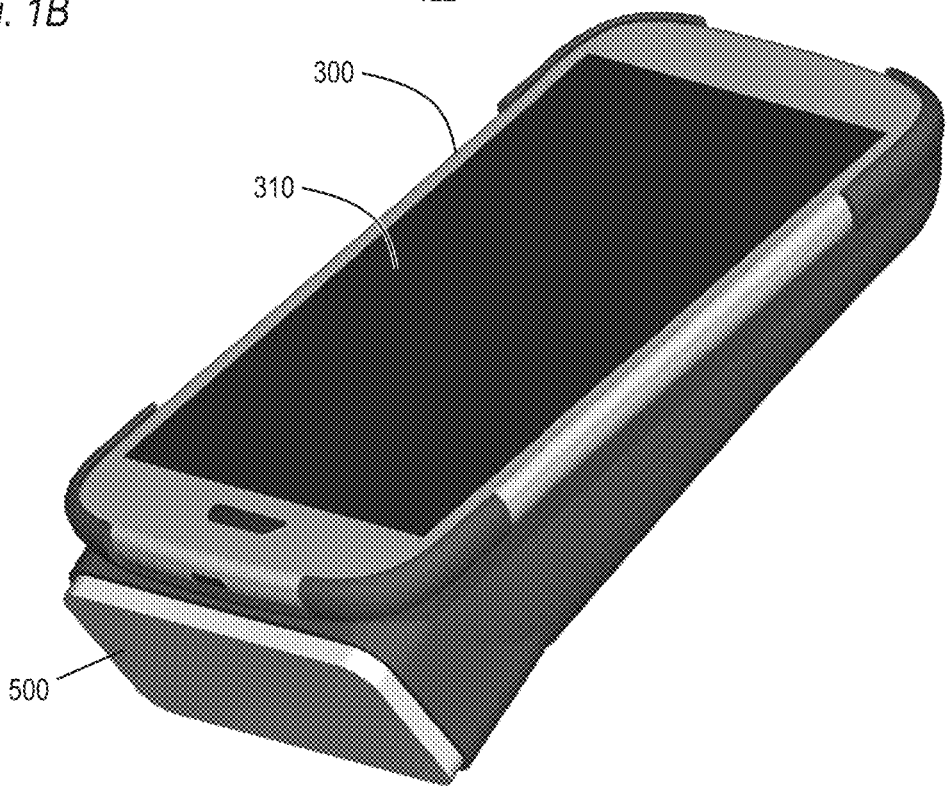
Figure 5:
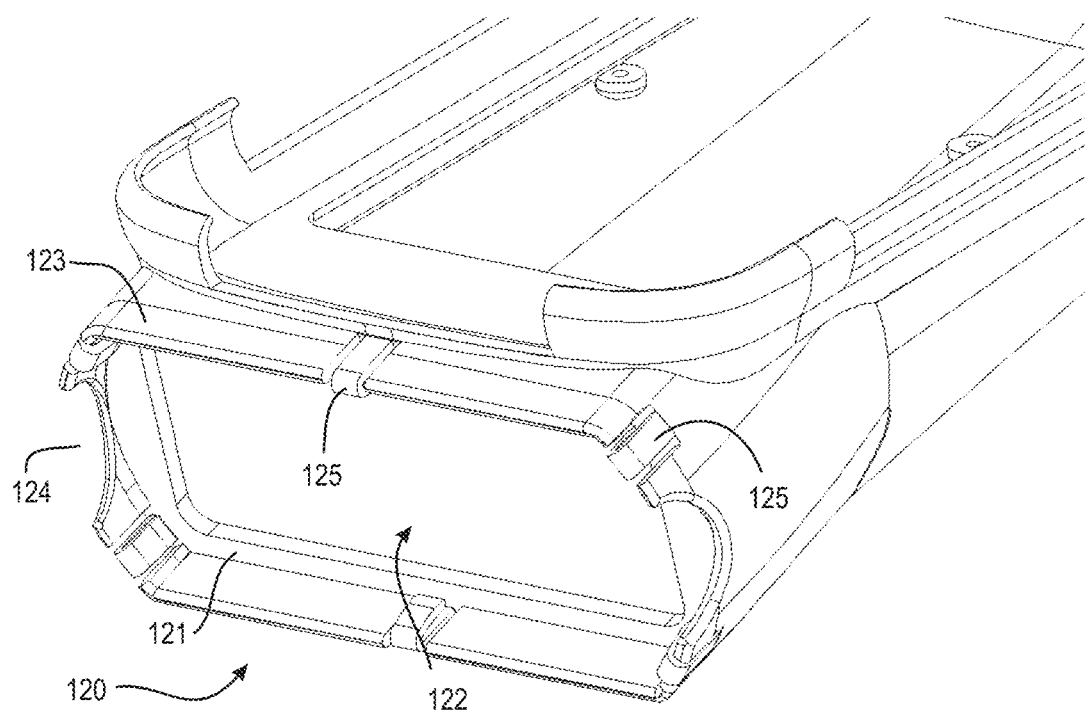
FIG. 5 illustrates a second receptacle according to an embodiment.

As shown in FIGS. 1A and 1B, the first receptacle 110 substantially covers or forms one side of the housing 100. Adjacent to a lower side of the first receptacle, which is in FIGS. 1A and 1B the left side, a second receptacle 120 is formed which is adapted for receiving a cartridge 500 either directly or through an adapter which can include a cartridge interface arranged within the housing 100 and cartridge holder. The adapter will be described further below. The second receptacle 120 includes a large opening 122 formed in a bottom wall portion 121 which forms an optical entrance to the internal space 102 of the housing 100. The bottom wall portion 121 forms a seating surface for the cartridge when inserted against which the cartridge abuts with its upper surface. FIG. 5 shows an enlarged view of the second receptacle 120.

Lateral side walls 123 surround the bottom wall portion 121 and include brackets 125 arranged at several positions which are integrally formed with the lateral side walls 123. In this embodiment, the brackets 125 are bars connected with the housing and extending parallel to the lateral side walls 123. The bars are folded back to the inner side of the second receptacle 120 to provide a free end 126 which presses laterally on the cartridge 500 when inserted so that the cartridge is kept by force-locking in the second receptacle 120. The folding-back structure provides sufficient flexibility and press force for allowing insertion, removal and reliable accommodation of the cartridge. At the same time, the cartridge remains pushed with its upper surface against the bottom wall portion 121 of the second receptacle 120.

Recesses 124 are formed in the lateral side walls 123 of the second receptacle 120 to allow the user to grab the cartridge for removal. Since the free ends 126 of the brackets are laterally to the cartridge, the free ends 126 slide along the lateral surfaces of the cartridge during insertion and removal. Slight lateral swinging movement may be used to overcome the frictional force exerted by the bracket 125 during removal.

The brackets 125 form elastic holders for keeping the cartridge in place.

The mobile device 300 is typically a smart phone as shown in FIG. 1B. Smartphone 300 includes a body, a touch-sensitive display 310, a camera including an imager, a light source, a CPU and a memory. The camera and the light source are formed on the backside of the smart phone and are therefore not visible in FIG. 1B. The smart phone 300 also includes a wireless interface for connecting to and communicating with a wireless network such as a WLAN or a cellular network. Further wireless interfaces are Bluetooth interfaces or NFC.

Figure 2A:
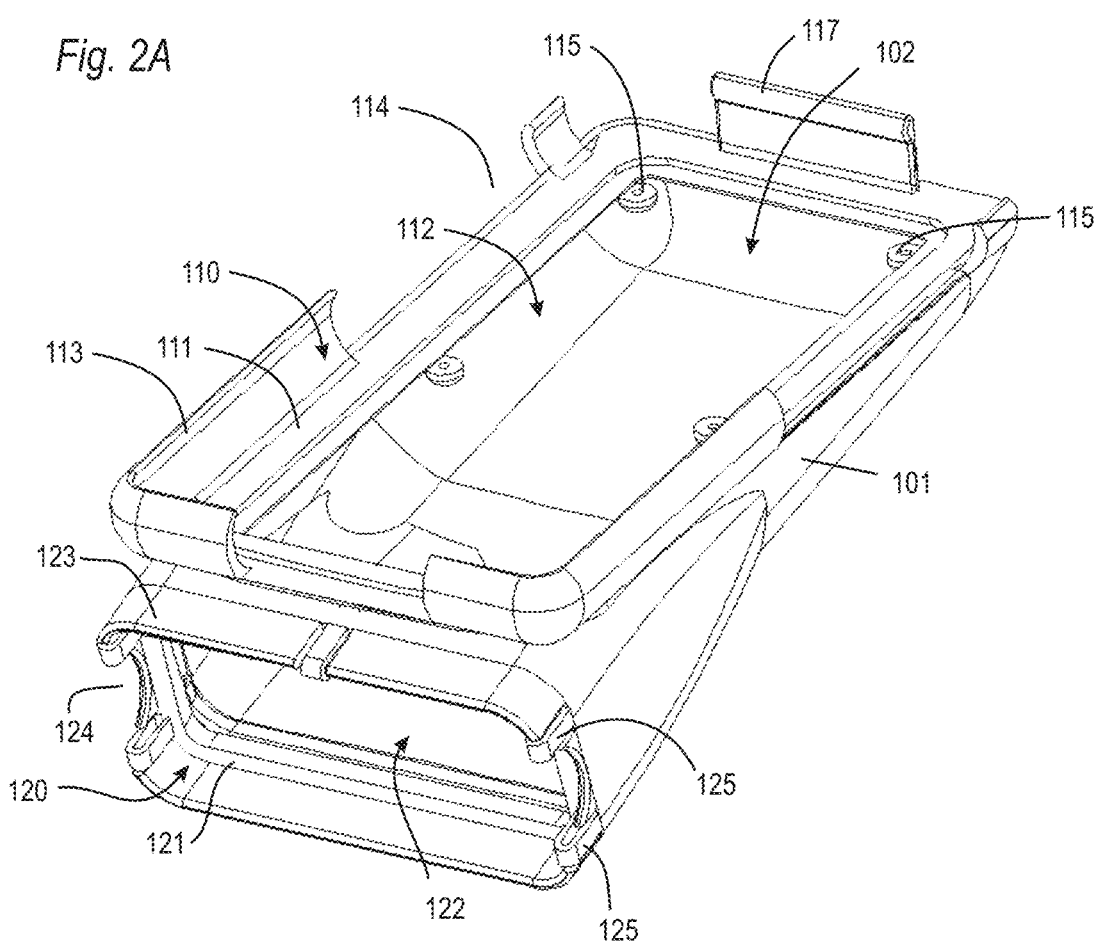
FIGS. 2A and 2B illustrate a portable reader module according to an embodiment.
Figure 2B:
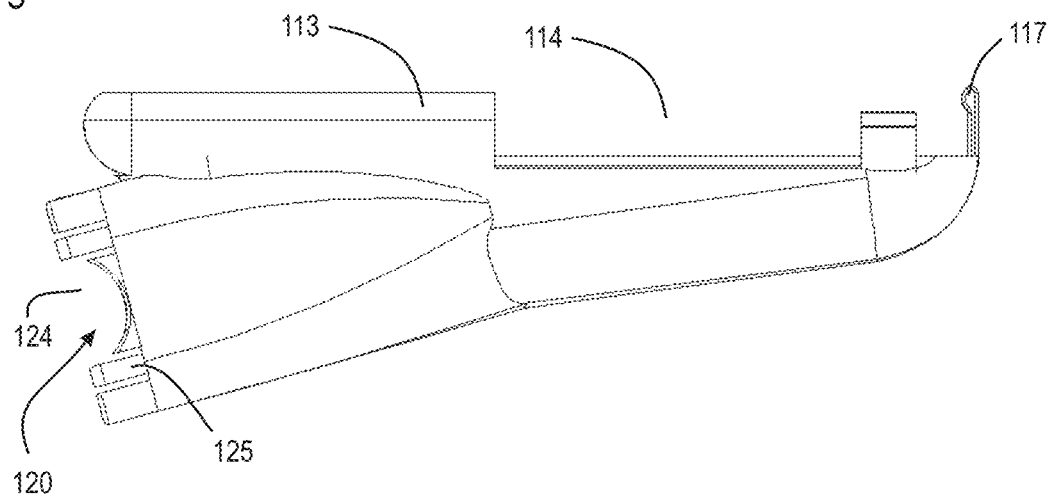
Figure 6:
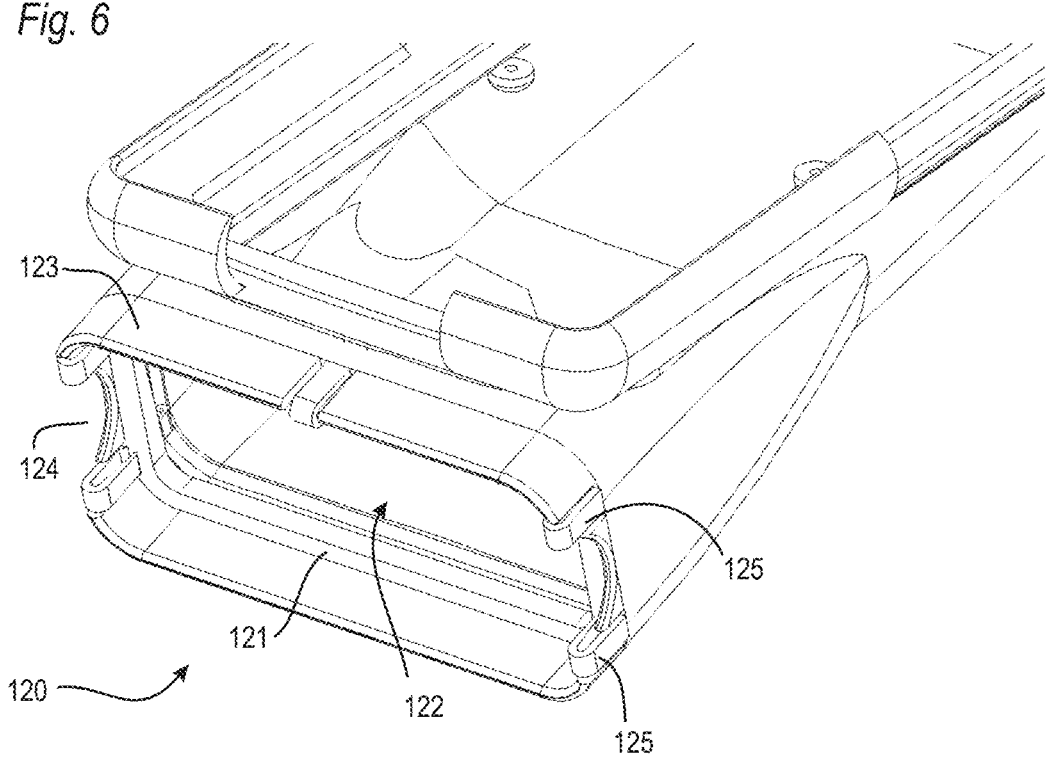
FIG. 6 illustrates a second receptacle according to an embodiment.

With respect to FIGS. 2A, 2B and 6 another embodiment of a housing 101 of a portable reader module is shown. FIG. 6 shows an enlarged view of the second receptacle 120. The housing 101 substantially corresponds to the housing 100 with some modifications made to the first and second receptacles 110, 120, respectively.

The lateral side walls 113 of the first receptacle 110 do not cover or surround the upper corners of the mobile device but only the top side and upper portions of the lateral side of the mobile device. Similar to the housing 100, the lateral side walls 113 surround the lower two corners of the mobile device. Furthermore, as best shown in FIG. 2B, the lateral side walls 113 have a convex form with the convex part facing to the interior of the first receptacle 110. The convex form, as in the embodiment of FIGS. 1A and 2B, engages around the sides of the mobile device to keep it in place.

Instead of having a convex shape, when see in cross section, the lateral side walls can be straight with a bulge 117 formed at the free end of the lateral side wall 123 at the upper part (left side in FIG. 2A) as shown in FIGS. 2A and 2B.

As already explained above, the first receptacle 110 is adapted for receiving a specific mobile device. Since the arrangement of the buttons, the size and shape are different for different models, the first receptacle 110 including its lateral side walls 113 varies for the different models of mobile devices.

Furthermore, as the size and shape of the cartridge are vendor-dependent, the second receptacle 120 is typically adapted for a given type of cartridge. In FIG. 2A, the short lateral sides of the second receptacle 120 are straighter in comparison to the lateral sides of the first receptacle as shown in FIGS. 1A and 1B. Alternatively, an adapter can be provided which holds the cartridge 500 and which provides the interface between the second receptacle 120 and the cartridge 500.

Figure 3:
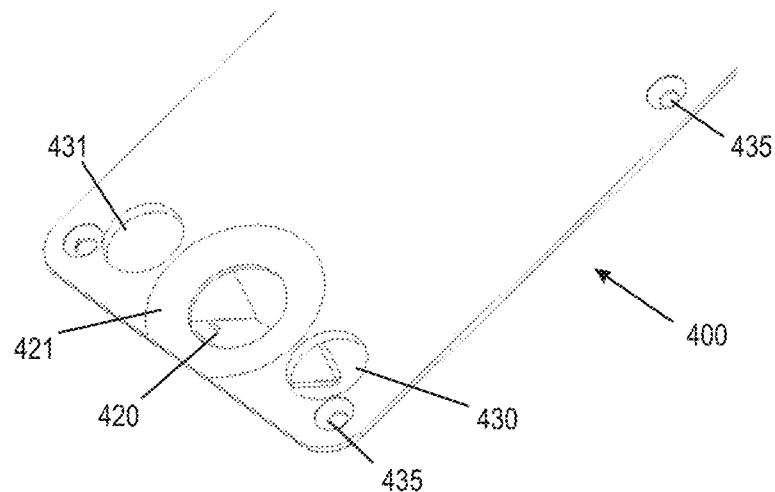
FIG. 3 illustrates a bottom element of a first receptacle according to an embodiment.
Figure 4A:
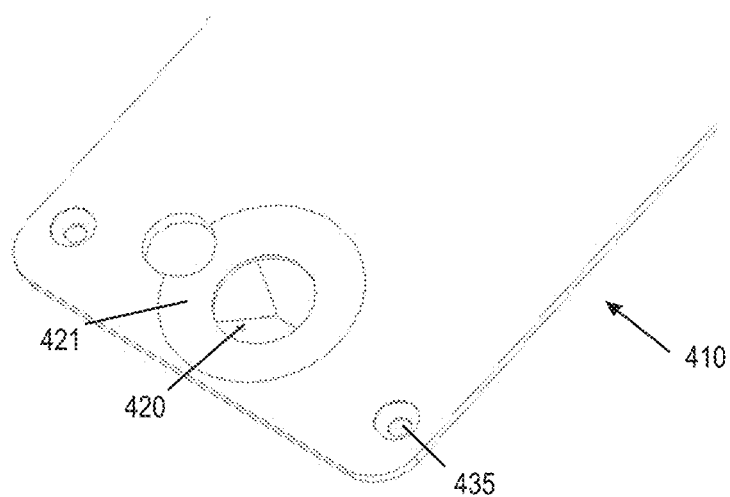
FIGS. 4A and 4B illustrates a bottom element of a first receptacle according to an embodiment.
Figure 4B:
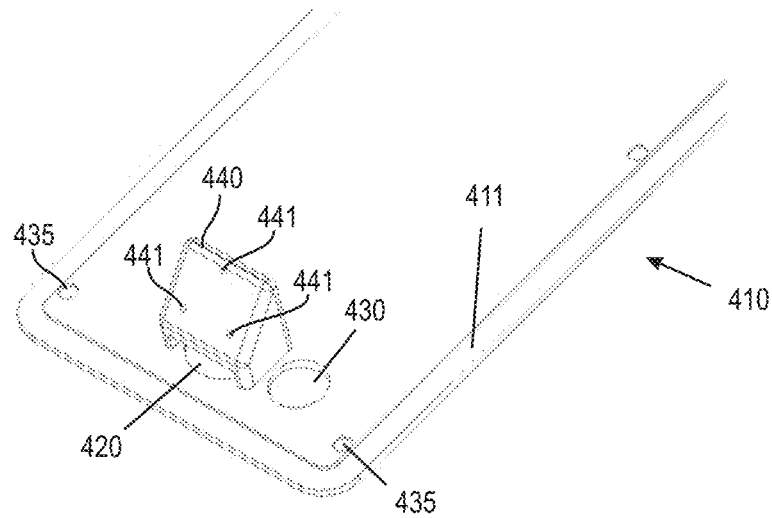

With reference to FIGS. 3, 4A and 4B, several embodiments of bottom elements are described. FIG. 3 illustrates a bottom element 400 which is formed as a flat plate. The bottom element 400 includes a main opening 420 arranged at a position which corresponds to the location of the camera lens of the mobile device when inserted into the first receptacle 110. Adjacent to the main opening 420, there are formed further openings 430, 431 which are provided for the light source or light sources of the mobile device 300. The bottom element 400 is thus adapted to the specific mobile device for which the first receptacle 110 is adapted. The bottom element 400 can be mounted to the housing 100, 101 by screws which are inserted into respective crew holes 435 which are in alignment with the female threads of the projections 115 of the housing 100, 101. Other ways of releasable mounting of the bottom element to the housing are possible such as use of elastic brackets that snaps into recesses.

When mounted to the housing 100, 101, the bottom element 400 closes the large opening 112 of the first receptacle 110. The openings 420, 430, 431 form the first optical entrance for the imager and the light source and can be covered by a transparent material for dust-prevention. The second optical entrance is formed by the large opening 122 of the second receptacle 120. Both the first and/or the second optical entrance can include a transparent material.

A recess or cavity 421 can be formed around the opening 420 to accommodate the lens of the mobile device when the lens projects from the back side of the mobile device.

FIG. 4A shows a further embodiment of a bottom element 410 including only an opening 420 for the camera lens and one opening 430 for the light source. While FIGS. 3 and 4A show the side of the bottom element 400, 410 which faces the mobile device 300, FIG. 4B shows the side which faces the internal space 102 of the housing 100, 101. As shown in FIG. 4B, a holder 440 is formed over the opening 420 for the imager for accommodating and holding a light-deflecting element which can be, for example, a mirror or a prism. The holder 440 is formed like a housing providing an opening facing to the right in FIG. 4B. The holder 440 also shields the light-deflecting optical element and the opening 420 from light emanating from the light source to minimise blending of the imager.

The opening 420 together with the holder 440 and the light-deflecting optical element are part of the optical path for capturing images of the cartridge.

The openings 430, 431 are part of the illumination path for illuminating the cartridge 500 using the mobiles device's optical source.

As further shown in FIG. 4B, a circumferentially running step 411 can be formed on the side of the bottom element 410 which faces the internal space 102. The step 411 is for aligning the bottom element 410 with the large opening 112 by engagement of the step 411 with the rim of the large opening 112 of the first receptacle 110. This ensure that the first optical entrance and the holder 440 are aligned with the first receptacle 110 and thus with the mobile device 300 when inserted.

The holder 440 for the light-deflecting optical element can include adjusting means which allows adjustment of the relative location and/or orientation of the light-deflecting element with respect to the holder 440. For example, screws can be inserted into the threads 441 formed on a rear wall of the housing 440 as shown in FIG. 4B. In the present embodiment, three threads arranged on corners of a triangle allow tilting of the light-deflecting optical element in three dimensions. The light-deflecting optical element can be spring-biased accommodated against the internal surface of the rear wall of the housing 440 for this purpose. Other options for allowing adjustment of the light-deflecting optical element are also possible, for example using a frame with tiltable elements.

Figure 9:
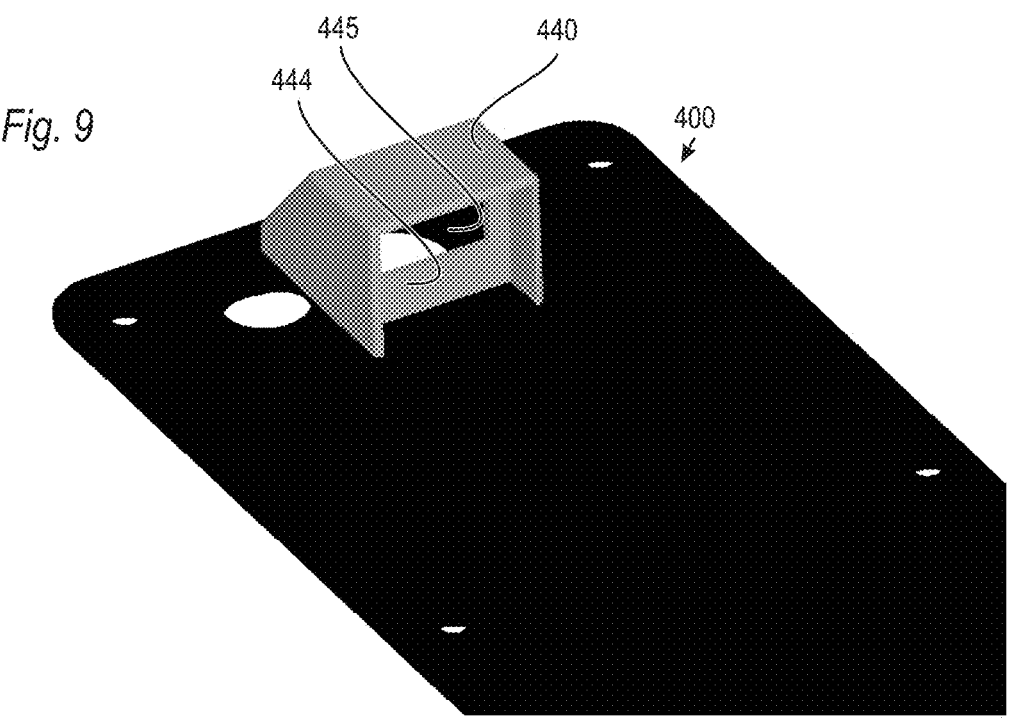
FIG. 9 illustrates a bottom element for a first receptacle according to an embodiment.

FIG. 9 shows the side of the holder 440 facing towards the cartridge 500. An internal wall 444 having an opening 445 is provided in the holder 440 to further minimise direct light incidence from the light source or of unwanted reflected light.

Figure 10:
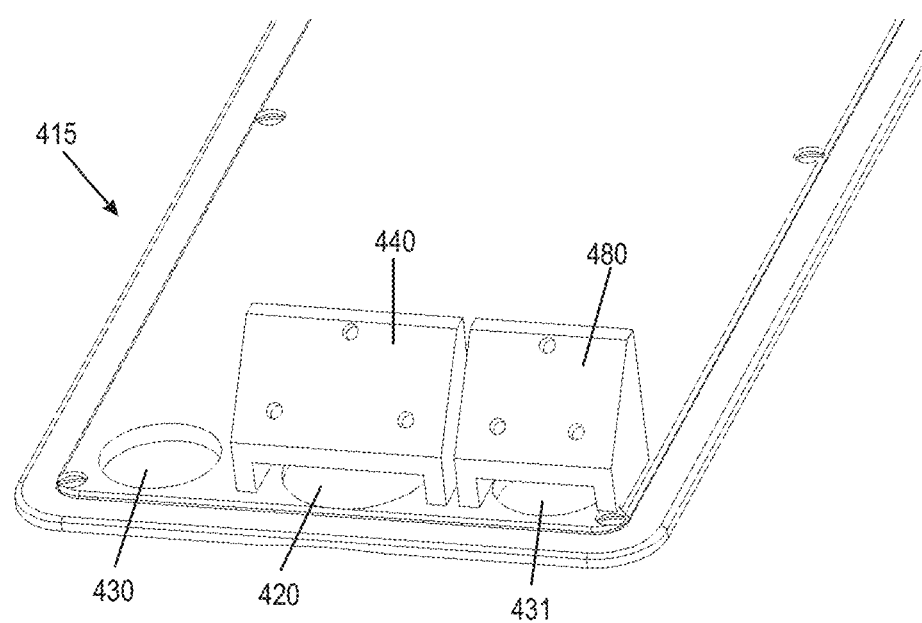
FIGS. 10 and 11 illustrate a bottom element of a first receptacle according to an embodiment.

FIG. 10 shows another bottom element 415 which includes, besides the holder 440 for the light-reflecting optical element for the optical path, a holder 480 for a reflector which is part of the illuminating path. Specifically, the holder 480 is arranged above the opening 431 which provides an optical access for the light of the optical source of the mobile device. The reflector is arranged internal of the holder 480.

Figure 11:
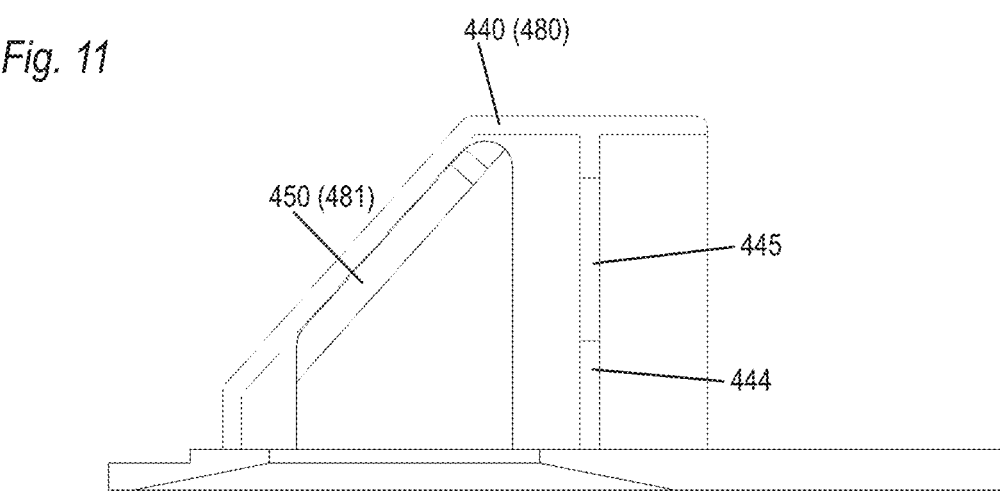

FIG. 11 illustrate a cross-sectional view of a holder 440 which can also be holder 480. The holder 440, 480 supports and carries the respective optical element such as the light-deflecting optical element 450 or a reflector 481 of the illuminating path.

Figure 7:
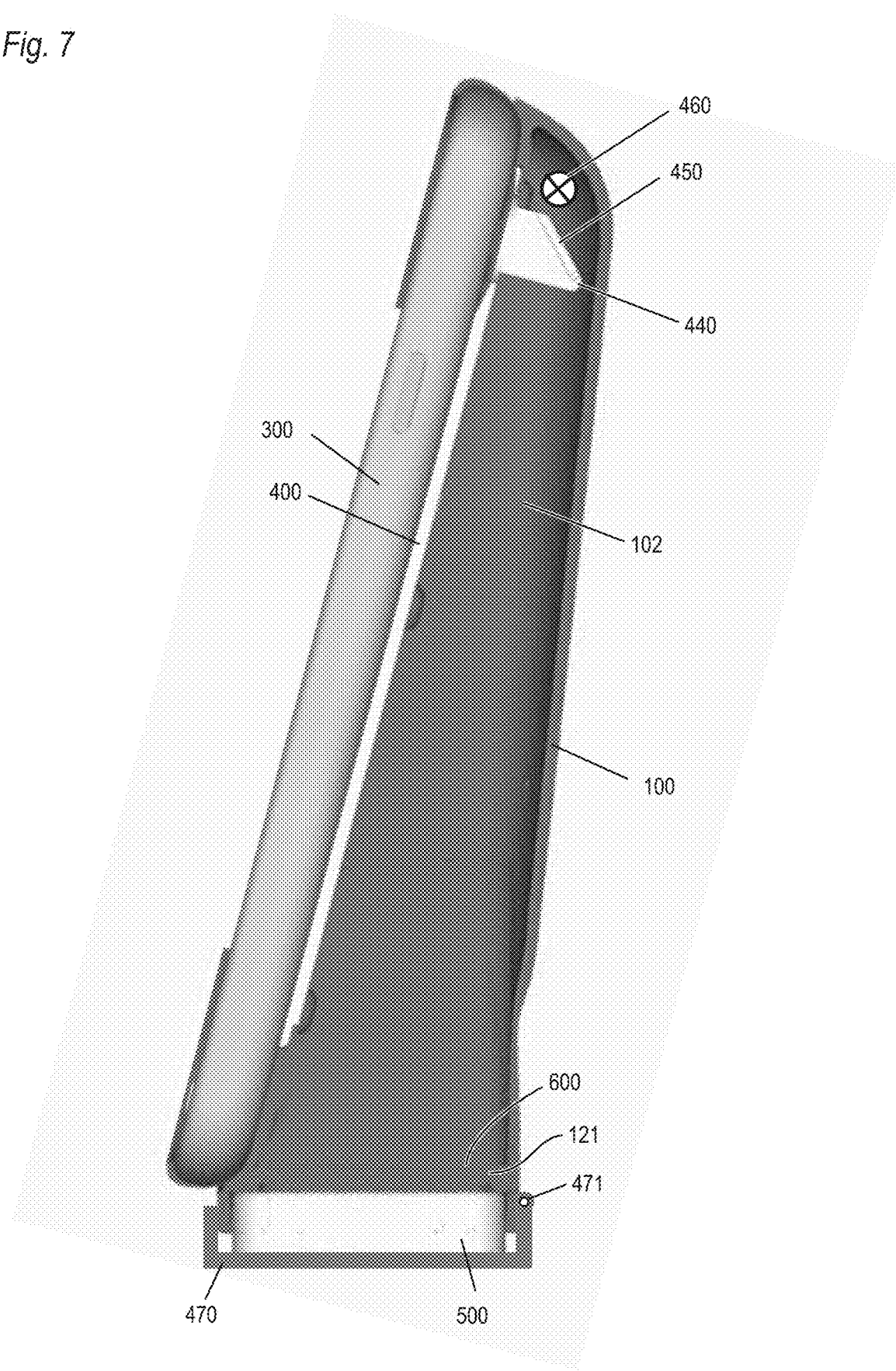
FIG. 7 illustrates cross sectional view through a portable reader according to an embodiment.

FIG. 7 shows a cross-sectional view through a portable reader arranged in an upright position. The cartridge 500 is inserted into the second receptacle 120 and allows the housing 100 to be placed in an upright position so that the mobile device 300 is slightly inclined with respect to the vertical axis. As can be gathered from FIG. 7, the centre of gravity of the mobile device 300 is approximately above the middle of the cartridge 500 to ensure mechanical stability when the portable reader stands on the cartridge 500. The titling angle is about 13 to 16° in this embodiment. Other tilting angles are also possible and can be chosen according to specific needs. The tilting angle is defined by the relative orientation of the first receptacle 110, defining a first plane, to the second receptacle 120, defining a second plane. Typically, the tilting angle can be between 10 and 20°, without wishing to be limited.

As shown in FIG. 7, the bottom element 400 holding the holder 400 with the light-deflecting optical element 450 abuts the back side or back surface of the mobile device 300 so that the mobile device 300 has the same orientation as the bottom element 400. The imager including the optical lens of the mobile device are opposite the holder 440 and the light-deflecting optical element 450 which allows the imager to capture an image of the cartridge 500.

As can be gathered from FIG. 7, the holder 440 including the light-deflecting optical element 450 is not arranged centrally above the cartridge 500 due to the inclination of the mobile device 300. Hence, the image captured by the imager can be tilted to some degree. This is, however, not critical as the mobile device 300 is equipped with algorithm allowing reliable detection of the regions of interest.

The optical path for capturing an image is thus bent or flexed allowing the cartridge 500 to be placed under an angle and, for example, at a lower end of the mobile device 300 while keeping the housing 100 compact.

The illumination path can also be bent similar to the optical path. Typically, the illumination path is different to the optical path so that a direct light entrance from the light source of the mobile device into the imager is prevented. For example, when the light source is arranged adjacent to the imager, the light striking the inner walls of the housing 100 in close proximity to the light source is reflected partially towards the imager. The holder 440, formed as a housing in this embodiment, shields the imager against the reflected light.

Figure 8:
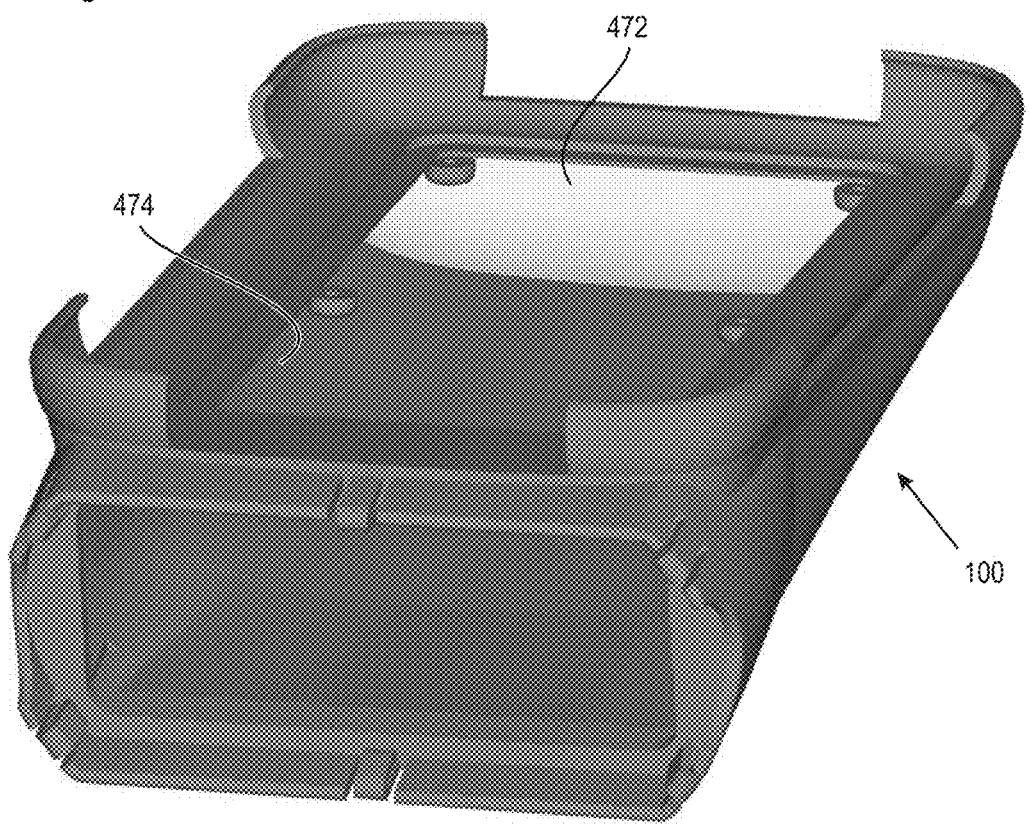
FIG. 8 illustrates a 3-dimensional view of a portable reader module according to an embodiment.

To reflect the light from the light source of the mobile device 300 to the cartridge 500, the upper part of the walls of the internal space 102 can be provided with a highly reflective surface while other parts of the inter space 102 are provided with a low-reflecting surface. This is illustrated in FIG. 8 showing the inner upper part of the internal space 102 provided with a white and highly reflective coating 472. The lower part is provided with a low reflecting coating 474, or the dark coloured material of the housing is provided with a diffuse reflecting finish.

When using the light source of the mobile device, no externally powered light sources that are powered, for example by the USB port of the mobile device, are needed. Thus the handling is simplified significantly.

Alternatively, or in addition to the light source of the mobile device 300, a light source 460 can be arranged in the internal space 102 of the housing 100, for example above or are laterally adjacent to the holder 440 so that the holder shields the imager against direct light exposure. The light source 460 can be powered by the mobile device. For example, a connector can be integrated into the first receptacle which provides electrical connection to the mobile device. Alternatively, an extra battery can be provided, or a battery holder can be integrated into the housing.

Typically, the cartridges 500 are made of a non-transparent material so that, when the cartridge 300 is inserted into the second receptacle 120, the second optical entrance is closed. When the cartridge 500 is made of a transparent or semi-transparent material, shielding the internal space 102 from ambient light can be ensured by a cover or cap 470 which can be connected to the housing 100 by an articulation or hinge 471 to allow the cap 470 to be slipped over the inserted cartridge 500 and the outer side of the second receptacle 120. FIG. 7 illustrates a cap 470 which can be swung around a horizontal axis which is parallel to the lateral orientation of the inserted cartridge 300.

In order to capture an image with the imager in the closed housing 100, a light source and the light-deflecting optical element 450 is used. The light source can be an internal flash light of the mobile device such as a smartphone, an internal torch light of a smartphone, a light source (LED, Bulb, OLED, laser diode . . . ) integrated in the housing 100 with power supplied by the smartphone or a smartphone-independent power supply in the housing.

The light-deflecting optical element can be a mirror, a prism, a concave mirror, a lens system, a reflective coating and or special shaping of the housing interior to obtain the desired deflection and focusing of the light from the light source, or a suitable combination of the above. In addition to that, covering or shielding elements for restricting the area of direct illumination, for example shielding the camera lens and light-deflecting optical element can be provided within the housing.

The arrangement of the light source and of reflecting elements is chosen to achieve sufficiently strong and homogenous illumination of the cartridge including its test zone. Direct reflection from the reflecting element into the camera can be avoided by choosing a proper geometry of reflecting or mirror elements and by introducing proper screens for covering the light-deflecting optical element from direct exposure.

Figure 12:
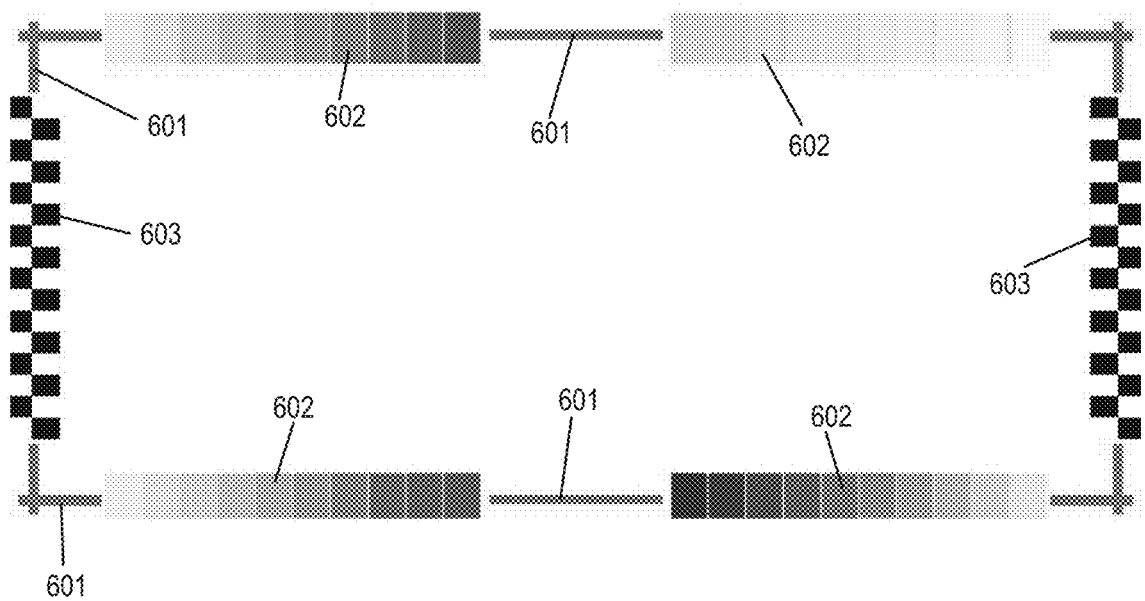
FIG. 12 illustrates optical reference elements according to an embodiment.

With reference to FIGS. 12 and 13A to 13C, optical reference elements are described. FIG. 12 shows a set of optical reference elements 600 which differ from each other in shape and/or colour. The optical reference elements 600 can be arranged within the housing 100 and particularly in close proximity to the second receptacle 120 and inserted cartridge 500. FIG. 7 shows that the optical reference elements 600 are arranged on the interior side of the bottom wall portion 121 of the second receptacle 120 which is provided with a window of a transparent material. The optical reference elements 600 can be printed onto a foil or sheet and form a passepartout around the region of interest.

First optical reference elements 601 are provided to allow the analysing algorithms the localisation of test regions. The first geometrical element 601 are positional elements includes crosses arranged in the four corners and lines.

Four different second optical elements 602 are also provided which are used as colour references and which are embodied as colour scales.

Third optical reference elements 603 are provided as checkerboards used for black and white calibration.

The above described optical reference elements 601, 602, 603 are used for specific purposes and are thus specifically adapted.

For example, the test zone of the cartridge is detected in the captured image automatically using robust algorithms. Using, for example the positional optical reference elements 601, a reliable detection of the test zone can be ensured. The mobile device can also run verification tests to check whether the correct regions have been detected. For example, for correct quantitative analysis of the test results, the location and the size of the test results regions are finally detected. To ensure this, the above mentioned plural optical reference elements are provided. This is different to commonly known approaches which only allow a partial or only semi-quantitative analysis.

A specific example of an analysis is described in connection with FIG. 13A to 13C.

Figure 13A:
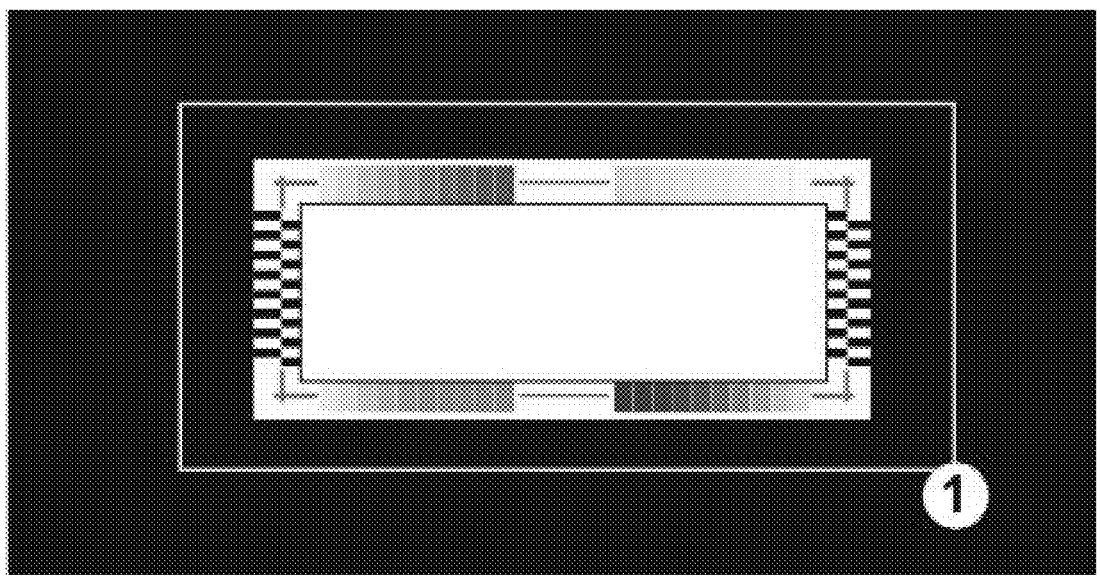
FIGS. 13A to 13C illustrates procedures of the quantitative analysis including calibration and quantitative evaluation according to an embodiment.

FIG. 13A shows an image captured by the mobile device without an inserted cartridge. The pre-tests and calibration can be run before the actual measurements, but can also be done when capturing an image of an inserted cartridge since the optical reference elements 600 remain visible.

In a first process, a coarse cut of the captured image is carried out. Providing the walls of the internal space 102 with low reflecting surfaces, at least in proximity to the second receptacle, facilitates this coarse cutting as the regions outside the optical reference elements 600 remain black. The frame marked at 1 corresponds to the coarse cutting frame. The coarse cutting process also takes advantage of the optical reference elements 601, 602, 603 within the image as these elements are known so that their identification is reliable.

As described above, each image captured by the mobile device includes the optical reference elements 600 as these elements are arranged within the housing and are visible for the imager irrespective whether the cartridge has been removed or not.

Before the coarse cutting process, image pre-processing can be carried out such as rotation or mirroring of the image as the image, due to the light-deflecting optical element, is upside down. Furthermore, the image data can be converted into a format suitable for further processing. For example, a suitable image data format is a YUC format such as YUV420 with Y referring to luminance and U/V referring to chrominance. Use of other date formats is also possible.

Figure 13B:
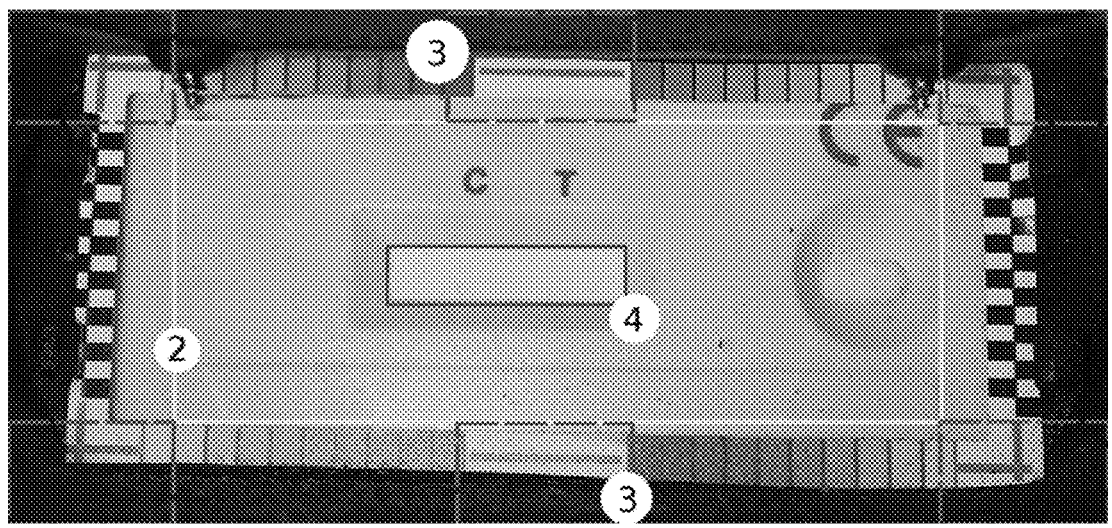

In a further process, the pre-processed image is subjected to a cropping process to identify the test zone in FIG. 13B. The regions marked at 3 indicate the first optical reference elements 601 which are used for this purpose. The positional algorithms are able to identify these optical reference elements and also the crosses in the corners. The specific colouring of the first optical reference elements 601, in the present embodiment with cyan colour, further facilitates detection of the first optical reference elements 601 in the image. Once these elements have been identified, the algorithm places a reference rectangle, marked at 2, in an inner region of the first optical reference elements 601.

The crosses of the first optical reference element 601 in the four corner of the image are used to define the left and right edges of the reference rectangle 2 while the lines of the first optical reference element 601 are used to define the upper and lower edge of the reference rectangle 2. The detection of the edges based on different optical reference elements reduces the identification process to 1-dimensional problems which can be handled faster and more reliable than 2-dimensional problems.

The cropping process continues using the identified rectangle 2 to search for the test zone indicated at 4. Since the reference rectangle 2 already defines an inner region of the cartridge, test zone 4 can be reliably detected even when the test zone 4 does not significantly differ from surrounding region in colour.

The first optical reference element 601, once detected, is used as positional calibration component for localising the test zone. Coloured optical reference elements, once identified, are used colorimetric calibration component which can also be used for localising structures such as the test zone.

In a further process, the pre-localised regions are displayed to the user prompting for confirmation whether the regions have been correctly identified. For example, the image as shown in FIG. 13B can be displayed on the display of the mobile device with the localised regions marked by coloured lines and rectangles.

The search for the test zone 4 can also be based on geometrical entities specific for the test result regions such as the shape and colour of the test result regions.

Once the test zone 4 has been identified, optionally confirmed by the user, quantitative evaluation of the test result regions starts. The embodiment shown in FIG. 13C includes two test result regions, one marked by T and the other marked by C with C meaning control and T meaning test. The process scans along at least one virtual line passing through test result region C and test result region T. The thus obtained 1-dimensional luminescence signal is indicated in FIG. 13C. The quantitative evaluation further includes trend correction of the luminescence signal to eliminate uneven illumination conditions. This can be done, for example, by using a high pass filter. Furthermore, the standard deviation can be calculated in regions outside the test result region C to allow derivation of a background threshold. In a further process, the luminescence signal is smoothed in the test result region C. This also allows detection of the geometrical width of the test result region C. Based on the correct localisation of the test result region C, the other test result region T is identified and processed as above. The thus identified and processed luminescence signal is used for quantitative evaluation, for example relative to the test result region T. The chrominance and luminance, if needed, can be accessed against the optical reference elements 602 as these reference elements 602 include chrominance and luminance values.

For improving the reliability of the quantitative evaluation, two or more line scans can be used. FIG. 13C indicates two line scans shown at 13 and 14, respectively.

Figure 13C:
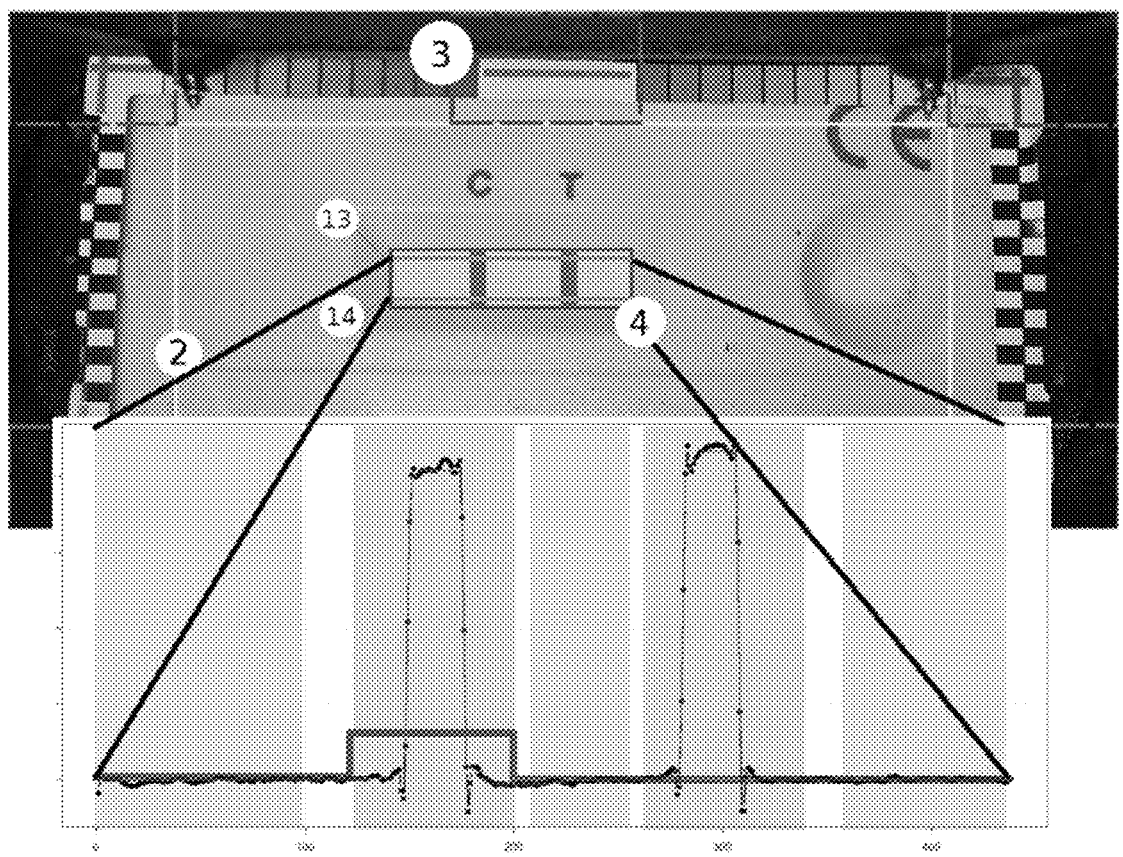
Figure 14:
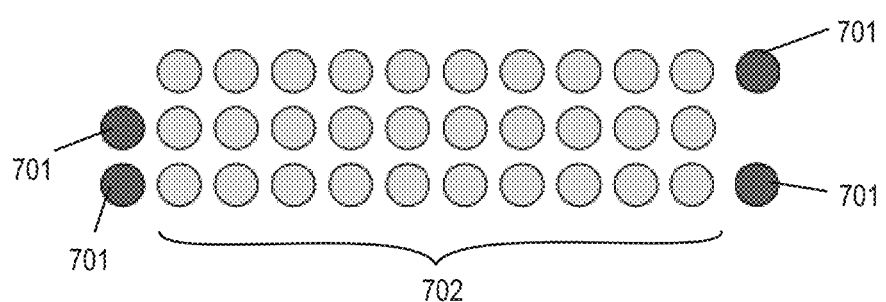
FIGS. 14 and 15 illustrates cartridges with multi-spot test result regions.
Figure 15:
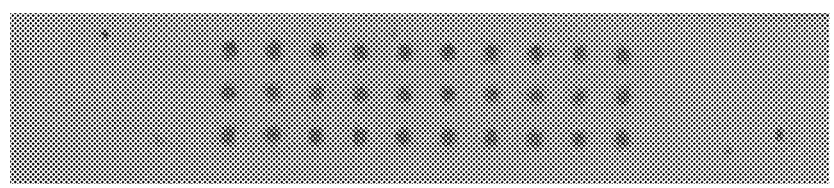

If only one test result region is provided, such as shown in FIG. 13C, the chrominance evaluation is not needed. On the other hand, when multiple test result regions are included by the cartridge, such as illustrated in FIGS. 14 and 15, not only the saturation of the colour is of interest but also the colour and any change in colour. FIG. 14 shows an embodiment having four reference spots 701 and an array of several test spots 702. FIG. 15 shows a real image of the test spots 702.

In an embodiment, software preloaded to the portable device such as smartphone uses one or several optical references contained in the housing to determine a quantitative or semi-quantitative evaluation of the test areas, perform a self-test or a calibration of the device. The optical reference elements are placed inside the housing in such a way that the imager can take an image of them simultaneously with the imaging of the test zone or test result region or separately.

The optical reference can include any combination of reference structures, scales, patterns, coloured areas, printings, stickers or labels within the housing. Using image analysis algorithms the software uses optical references like crosses, lines and checker boards for positional references and determines the precise position of the test area or of further optical references within the image or images taken by the imager. Positional references are typically used as the imager does not need to be a integral part of the module reader but rather of the removable portable device and thus be subject to poor positioning within the designed optical path.

A possible intensity reference is any area with defined reflectivity or transmittance including gray scales and gray step wedges or checker broads, line pattern and noise pattern. A possible colour references is any area with defined reflectivity or transmittance such as colour like colour scale, colour step wedge or optical elements like prisms or gratings.

The evaluation of test result regions includes any combination of the following processes:

determination of the position and possibly shape or outline of the test result regions using prior obtained information on positional markers or segmentation algorithms;

evaluations of colour or intensity employing one or several methods for pixel wise or area wise colour or intensity characterization like signal, intensity, background, difference to background, noise level, signal to noise ratio;

evaluation, pixel, area, shape or size wise comparison with colour or intensity references (in the housing).

Self-testing of the portable device is achieved by comparing the obtained positions determined for positional references, by evaluations provided for the intensity references as well as colour, colour distribution or colour intensities, evaluations (e.g. on RGB, CYMK) provided for the colour references with values or intervals predefined in the software or software configuration. Meeting certain values or intervals is used as criterion to determine proper or improper system function.

If the portable device calibration is not yet achieved, one or several system parameters like lightning, imager position, cartridge position, image processing and image evaluation are changed and then the self-test is repeated until proper/desired system function is achieved or maximum number of repetitions is reached.

In another embodiment optical, references or additional optical reference especially for system self-test and system calibration can be provided by special reference cartridges. A reference cartridge is any cartridge that fits to the second receptacle and has structures, scales, patterns, coloured areas, printings, stickers or labels designed to be used as optical reference by the system.

In another embodiment, the test cartridge bearing the test zone can include one or more additional optical reference elements for testing a verification such as bar codes and other markers.

The quantitative analysis can relate to biomarker detection or to medical, biological, chemical environmental and other markers. The above described tests can evaluate single or multiple or heterogeneous marker addressing medical chemical environmental life style related or marker used in personalized medicine.

The above described modular reader especially enables a quantitative evaluation of specified test cartridge. By using suitable calibration procedures performed according to specific specifications, a relative or absolute quantification of the test signals can be achieved.

The analyte test can take place in a commercial cartridge as used for lateral flow assays or in other formats having a suitable viewing window allowing the optical evaluation and using internal or external micro fluidics applications.

The portable reader is capable of evaluating chemical, enzymatic, colorimetric or natural coloured probes.

The portable reader is suitable for the detection of single or multiplexed assays.

The test which can be carried out as described above results in a quantitative determination of one or more similar or different kinds of marker molecules, typically biomarkers (e.g. Strep A). Further tests refer to the quantitative analysis of histological sections, 2-dimensional gel tests or multi-spot assays.

A portable reader module according to a further embodiment is illustrated in FIGS. 16 and 17. FIGS. 16 and 17 are partially cut-away to allow illustration of the internal structure of the elements.

The portable reader module includes, in addition to the configuration of the portable reader module shown in FIGS. 1A and 2B, an adapter 705. The adapter 705 includes a cartridge interface 710 and a cartridge holder 720. The cartridge interface 710 is releasably inserted into and fixed in the second receptacle 120.

The cartridge interface 710 has an outer shape that corresponds to the inner size and shape of the second receptacle 120 so that the cartridge interface 710 is firmly held in the second receptacle 120 when inserted. The cartridge interface 710 can be fixed in the second receptacle 120 by a press fit or by an adhesive. A releasable fixation, for example by elastic elements which engages with the cartridge interface 720, can also be used.

The cartridge holder 720 has a bottom wall 726 and side walls 725 extending from the bottom wall 726 to define a cavity 721. The cavity 721 is open at a side opposite the bottom wall 726. The cavity 721 is large enough to accommodate the cartridge 750 which can be inserted into the cavity 721 of the cartridge holder 720. The cartridge holder 720 in FIG. 17 is partially cut away to allow visualisation of the cavity 721.

The size and shape of the cavity 721 can at least in sections correspond to the lateral outer size and shape of the cartridge 750 so that the cartridge 750 is held in a given position within the cavity 721 of the cartridge holder 720. In addition to that, or alternatively, adjusting elements which engages with the cartridge 750 when placed into the cartridge holder 720 can be provided in the cavity 721, for example on the inner side of the side walls 725 and the inner side of the bottom wall 726. This inner side refers to the side facing the cartridge 750.

As best shown in FIG. 17, the cartridge interface 710 has a large central opening 711 which allows illumination and observation of the cartridge 750. The cartridge interface 710 can be basically ring-shaped. An outer step 716 is provided which forms a stop for the cartridge interface 710 when inserted into the second receptacle 120. Alternatively, the housing 100 can include an internal stop formed e.g. by the bottom wall portion 121 as shown in, for example, FIGS. 5 and 6. In this case, the outer step 716 is not needed and the cartridge interface 710 can be completely inserted into the second receptacle 120 and does not project the lower end of the housing 100.

The outer rim of the step 716 also functions as alignment element for aligning the cartridge holder 720 relative to the cartridge interface 710. The upper portion of the inner side of the side wall 725 of the cartridge holder 720 surrounds and cooperates with the step 716 for alignment purposes. In addition to that, the cartridge 750 abuts the lower face of the cartridge interface 710. As the cartridge 750 is aligned relative to the cartridge holder 720, the cartridge 750 is also aligned relative to the cartridge interface 710 by cooperation of the cartridge holder 720 with the cartridge interface 710.

As illustrated in FIGS. 16 and 17, the cartridge 750 is smaller than the cartridge holder 720 and can therefore be completely accommodated within the cavity 721 of the cartridge holder 720. The cartridge holder 720 can therefore completely surround the outer periphery of the cartridge interface 710, and portions of the second receptacle 120, to provide a light-tight connection. The embodiment of FIGS. 16 and 17 is suitable for small cartridges.

As illustrated in FIGS. 16 and 17, the cartridge interface 710 includes the step 716, which can also be referred to as outer lateral projection, to form a stop when pushing the cartridge interface 710 into the second receptacle 120 and to improve light-tight closure of the second receptacle 120 to prevent that stray light can enter the internal space 102 of the housing 100. The step 716 can also form an alignment element for cooperation with the inner peripheral walls of the cartridge holder 720. When the step 716 does not laterally project the outer periphery of the housing, lateral alignment of the holder 720 relative to the housing 100 is brought about by direct engagement of the outer periphery of the lower end of the housing 100 and the inner periphery walls of the cartridge holder 720.

The lateral alignment refers to an alignment in x- and y-direction. The x-direction is indicated in FIG. 16 while the y-direction points into the drawing plane. The x- and y-directions are parallel to the plane of the cartridge 750. The vertical alignment refers to the z-direction indicated in FIG. 16 which is perpendicular to the plane of the cartridge when the cartridge is inserted into the adapter 705 formed by the cartridge holder 720 and the cartridge interface 710.

In a variation, step 716 is not provided and the cartridge interface 710 is completely inserted into the second receptacle 120. In this case, lateral alignment is brought about by direct cooperation between the cartridge holder 720 and the housing 100.

The vertical alignment of the cartridge holder 720 relative to the cartridge interface 710 can be brought about by direct cooperation between the cartridge holder 720 and the cartridge interface 710, for example.

For holding the cartridge holder 720 firmly in place, the cartridge interface 710 includes magnetic bodies 712 which cooperate with metallic pins, discs or brads 722 of the cartridge holder 720 for (ferro-) magnetic coupling. For example, the cartridge interface 710 can include four magnetic bodies 712 each of which is arranged in one of the four corners of the cartridge interface 710. The magnetic bodies 712 are typically not exposed at the lower side of the cartridge interface 710 for protection. When using, for example, neodymium magnets the holding forces are large enough even when the magnetic bodies 712 do not come into direct contact with the pins or discs 722. The pins 722 can be made of a ferromagnetic metal or alloy.

The magnetic coupling can also bring about the vertical alignment, for example when the pins 722 abut the magnetic bodies 712. The lateral alignment is typically provided by the upper rim of the cartridge holder 720 facing the housing 100 when the inner peripheral wall portions of the upper rim surrounds and partially encompasses the outer periphery of the lower end of the housing 100. This also provides light-shielding of the internal space 102.

Both the cartridge interface 710 and the cartridge holder 720 can be made of a plastic material and manufactured by extrusion moulding or by an additive process. The pins 722 and the magnetic bodies 712 can be embedded in the material of the cartridge interface 710 and the cartridge holder 720, respectively.

The second receptacle 120 can therefore be designed to accommodate a separate adapter 705 which includes two separate parts, namely the cartridge interface 710 and the cartridge holder 720. The two parts 710, 720 accommodate the cartridge 750 from above and from below, respectively. A modular design of the cartridge interface 710 and the cartridge holder 720 enables accommodation of cartridges 750 of very variable size and geometry.

The cartridge interface 710 is typically designed to precisely fit into the second receptacle 120 of the portable reader module from below so that dust cannot enter the housing 100 and the internal space 102. Insertion of the cartridge interface 710 into the second receptacle 120 can be permanent or removable, for example for maintenance, but should in either case guarantee a defined and unchanging positioning of the cartridge with respect to the housing 100 and the mobile device. An additional sealing can be provided between the cartridge interface 710 and the second receptacle 120, and the cartridge holder 720 and the cartridge interface 710, respectively.

According to an embodiment, the cartridge interface 710 is permanently coupled to the second receptacle 120, for example by glue or an appropriate home-locking mechanism.

The cartridge interface 710 allows optical access to the test zone or test zones on the cartridge 750. The opening 711 of the cartridge interface 710 provides such an access which can be covered by a transparent glass panel for dust protection.

The cartridge interface 710 holds on its upper side, which faces the internal space 102, the optical reference elements used for calibration of the mobile device, so that these reference elements are positioned in proximity to the test zone or measurement area of the cartridge 750 which faces the internal space 102 of the portable reader module.

For operation, the cartridge 750 is placed into the cavity 721 of the cartridge holder 720 which is then brought into contact with the cartridge interface 710. The magnetic interaction between the magnetic bodies 712 and the metallic pins 722 of the cartridge holder 720 keeps the cartridge holder 720 firmly in place, so that the cartridge 750 is aligned relative to the second receptacle 120 and thus the mobile device.

After use, the cartridge holder 720 can be removed easily to allow replacement of the cartridge 750.

The cartridge holder 720 can be designed to be disposable, for example together with the cartridge 750.

According to an embodiment, the cartridge interface 710 can cooperate with different cartridge holders 720 designed for different cartridges 750. This allows using of different cartridges 750 without requiring different housings 100. The cartridge interface 710 can thus be a general interface for all cartridge holders 720 which facilitates use of the portable reader.

Figure 18A:
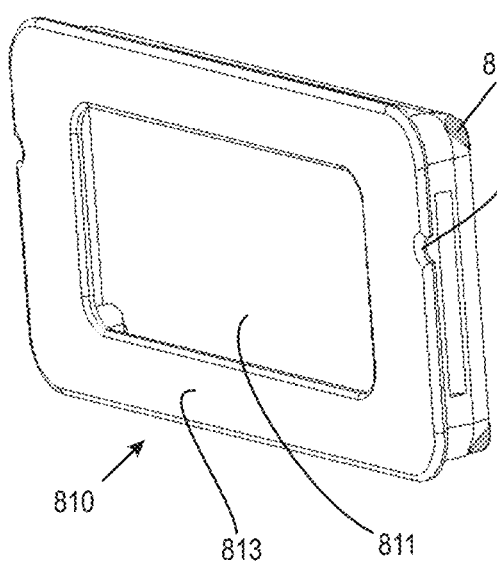
FIGS. 18A and 18B illustrates a cartridge interface according to an embodiment.
Figure 18B:
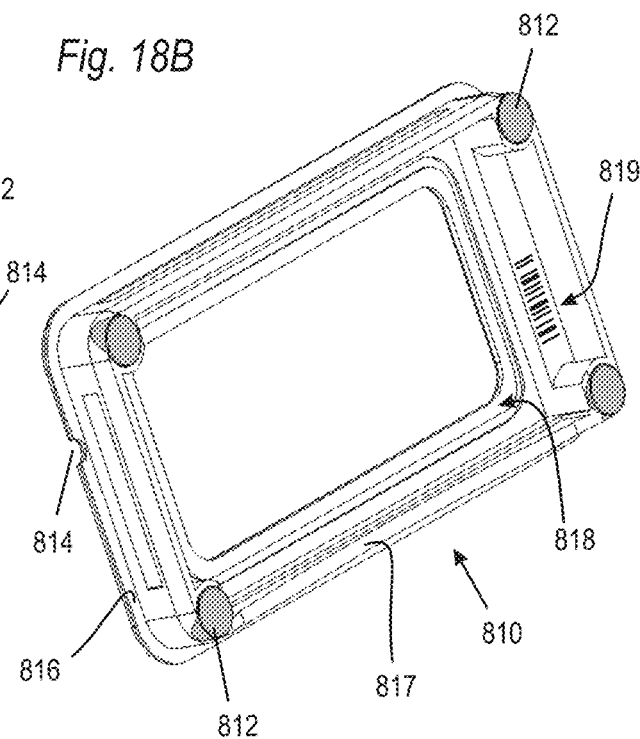
Figure 19:
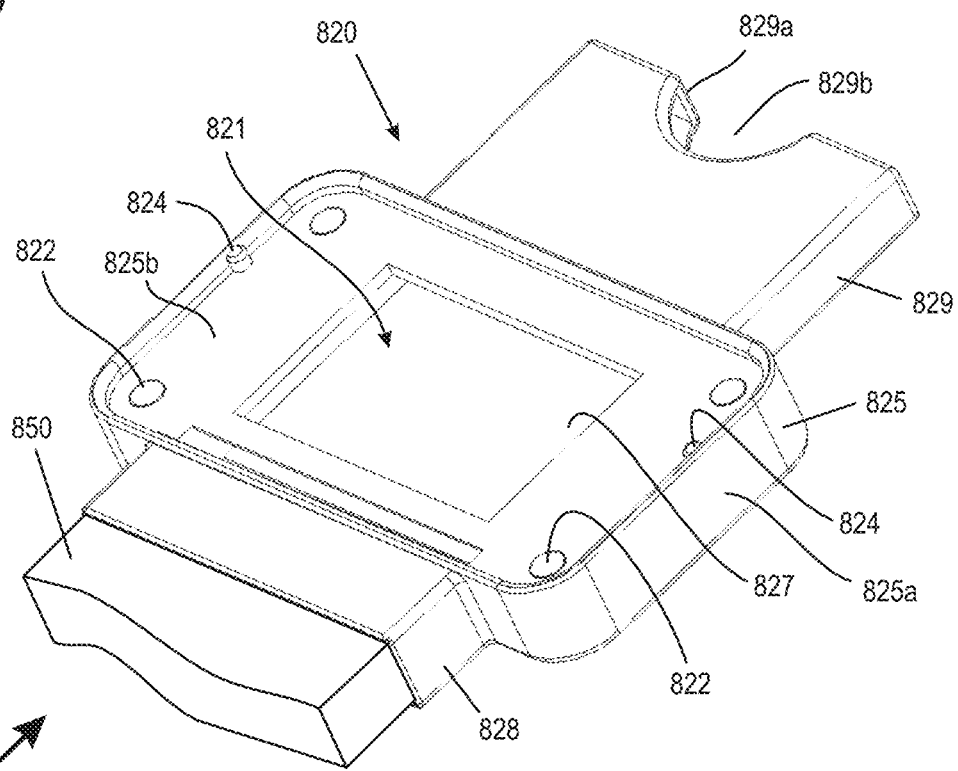
FIG. 19 shows a cartridge holder according to an embodiment.

FIGS. 18A, 18B and 19 illustrate a further embodiment. FIG. 18A shows a cartridge interface 810 from the side facing the cartridge holder 820 of FIG. 19, while FIG. 18B shows the cartridge interface 810 from the side which is inserted into the second receptacle 120.

The cartridge interface 810 includes a frame 817 having a ring-like wall with an outer periphery that corresponds to the inner periphery of the second receptacle 120 for frictional engagement with the second receptacle 120. To improve the fixation of the cartridge interface 810, an adhesive can be used.

The cartridge interface 810 further includes a lower wall 813 from which the wall of the frame 817 extends. The lower wall 813 slightly projects, in lateral direction, over the outer periphery of the frame 817 to form a step 816 which abuts the lower end of the housing 100 when the cartridge interface 810 is fully inserted.

The lower wall 813 has a large opening 811 to define the second optical entrance. On the inner side of the lower wall 813, a recess 818 is formed by the lower wall 813 and the frame 817 to accommodate an optical window for dust protection and one or more reference elements as described above. The reference elements can be directly formed on the optical window or can be on a separate transparent sheet which is placed on and held by the optical window.

Recesses 814 forming keying elements are formed at the laterally outer rim of the lower wall 813 for engagement with respective keying element 824 of the cartridge holder 820 as shown in FIG. 19.

Magnetic bodies 812 are arranged at each of the four corners of the frame 817. The magnetic bodies are moulded into the material of the cartridge interface 810 and are not exposed at the side of the lower wall 813 to avoid contact with chemical components contained in the cartridge or any other liquid.

An identification mark 819 can be arranged on the internal side of the cartridge interface 810 which faces into the housing 100 when the cartridge interface 810 is inserted into the second receptacle 120. The identification mark 819 is typically arranged close to the opening 811 and any reference element so that the identification mark 819 is within the field of view of the camera (imager) of the mobile device.

The identification mark 819 can be barcode, as shown in FIG. 18B, or any other mark which is optically recognizable by the mobile device. Other examples are colour code and an alphanumerical string. The identification mark 819 is unique for the particular cartridge interface 810 so that the cartridge interface 810 can be identified.

In addition to, or alternatively, a housing identification mark can be arranged within the housing 100, and typically close to the second receptacle so that the housing identification mark is within the field of view of the camera. The housing identification mark uniquely identifies the housing 100.

The cartridge holder 820, as illustrated in FIG. 19, includes a main body 825 formed by a lateral wall 825*a*, a top wall 825*b* and a lower wall opposite the top wall. The lower wall is not shown in FIG. 19. The lateral wall 825*a*, the lower wall and the top wall 825*b* enclose a part of a lateral channel extending along a transversal direction of the cartridge holder 820. A first projection 828 is formed at one lateral side of the lateral wall 825*a* and a second projection 829 is formed on an opposite side of the lateral wall 825*a*. Both projections 828, 829 are hollow and have a cross-section that allows insertion of a cartridge 850 as illustrated in FIG. 19. The first projection 828 has an entrance opening for the cartridge 850.

The cartridge 850 is inserted into the first projection 828 along the direction indicated by the arrow, passes through the main body 825 and extends into the second projection 829 where it finally abuts a wall 829*a* when the cartridge 850 is fully inserted. An opening 829*b* formed at a laterally outer end of the second projections provides access to the fully inserted cartridge 850 so that the user can push the cartridge 850 back to remove it from the cartridge holder 820.

The lateral channel is thus formed by the main body 825, the first projection 828 and the second projection 829. Together they form a cavity 821 for accommodating the cartridge 850. The internal walls of the cavity 821 are formed such that the cartridge 850 is aligned with respect to the cartridge holder 820 and held firmly in place therein. At the same time, the cartridge 850 is aligned relative to the cartridge holder 820.

The cartridge holder 820 further includes a window 827 which is formed in the top wall 825*b* of the main body 825. The window 827 basically corresponds to the large opening 811 of the cartridge interface 810 to provide optical access to the test regions or zones of cartridge 850 which are visible in the window 827 when the cartridge 850 is fully inserted into the cartridge holder 820. The measurement regions, i.e. the test zones 851, 852, of the cartridge 850 are then optically accessible from the internal space 102 of the housing 100.

To keep the cartridge holder 820 firmly in place, pins 822 are embedded in the main body 825 and exposed at the side of the cartridge holder 820 which faces the cartridge interface to allow magnetic coupling with the magnetic bodies 812 of the cartridge interface 810.

The lateral wall 825*a* of the main body 825 vertically projects the top wall 825*b* to form a ring-like rim which will engage the outer periphery of the housing 100 when the cartridge holder 820 is pushed on the lower end of the housing 100. The keying elements 824 formed within the rim ensure that the cartridge holder 820, and thus the cartridge 850, has the correct orientation.

The vertical alignment of the cartridge holder 820 relative to the cartridge interface 810 and the housing 100 is effected by the engagement of the top wall 825*b* of the main body 825 of the cartridge holder 820 and the lower wall 813 of the cartridge interface 810, or by the pins 822 and the lower wall 813 of the cartridge interface 810 when the pins 822 project the top wall 825*b* of the main body 825.

The lateral alignment of the cartridge holder 820 relative to the cartridge interface and the housing 100 is brought about by the cooperation of the ring-like rim of lateral wall 825*a* of the main body 825 with the outer periphery of the housing 100.

The cartridge interface 810 can be the same as in FIGS. 16 and 17, or can be a cartridge interface specifically adapted for the cartridge holder 820.

A process for adapting a workflow for calibration and/or quantitative evaluation is described below. The adaptation uses information which is linked with the identification mark, or which can be accessed from a database using the identification mark as database key.

The portable reader module includes one or more identification marks which uniquely identify at least one individual component or part of the reader module such as the holder for the light-deflecting optical element or cartridge holder. The identification mark or marks are arranged so as to be within in field of view of the camera of the mobile device. The identification mark is thus also included in the image captured by the camera.

The identification marks are suitable for automatic localization and interpretation by image analysis algorithms used by the mobile device's software. Suitable identification marks are barcodes. Examples are 1-dimensional codes such as the typical barcode or 2-dimensional codes of strips or dots such as the QR-code. Other examples are color codes or alphanumerical strings. The identification mark thus represents a symbolic textual identification string uniquely associated with each reader component encoded by the identification mark and decodable by the image analysis algorithms.

The unique symbolic textual identification is suitable for processing by further algorithms. For example, the unique symbolic textual identification can be a number.

In an embodiment, the identification mark will be a barcode attached to the reader component, for example inside the housing, and located in a pre-defined geometrical position of the image.

A database is provided which can either be a database stored in the mobile device or in a computer system external to the mobile device. The database can be represented by any entity which is organized to store and retrieve information. The database stores information on properties and/or configurations of the different reader components like the mobile device, housing, or cartridge interface. The mobile device's software has access to the database, for example by establishing a network socket or any other suitable communication channel.

The information stored in the database includes information on individual properties of the components which can be obtained during the manufacturing or assembly process for the portable reader module or when performing a comparison to one or more pre-defined references as employed in a calibration procedure. For example, manufacturing tolerances specific to each component can be stored in the database to facilitate the calibration procedure. This information is also referred to as calibration parameters.

The information on properties of the components of the portable reader module is stored in a database identifiable by a unique alphanumeric ID, which is associated with the identification mark, to allow processing by an algorithm. The unique alphanumeric ID represents a database key. The term "database key" is not limited to a key for a relational database but represents any identifier which can be used to retrieve information from the database such as a file system or a single file.

The mobile device includes an algorithm, for example embodied as software, which is able to (1) determine the identification IDs from the barcode; (2) to access the corresponding information in the database (3); and to use the information for properly parameterizing quantitative evaluation procedures as needed for test evaluation or for initiating a calibration when no parameters are stored.

Hence, the information obtained from the database is used to adapt the workflow for the calibration and evaluation procedures. Adaptation of the workflow includes selection of a workflow which can be specific for the type of cartridge and specific to the actually inserted cartridge interface. The adaptation can also include a change of the order of steps, or the omission or inclusion of specific steps. For example, when the calibration parameters are available, the calibration steps can be omitted. If not, the user can be guided through a calibration test, or automatically.

The information can also be used for parametrization of the quantitative evaluation procedure which can result in an alteration of the actions of the used algorithms. For example, the algorithm can act in different ways e.g. by controlling numeric calculations or by altering the control flow of the algorithm which can result in different sequences of user interaction.

The software and the algorithms may be constructed so as to build up a symbolic self-representation of all assembled reader modules possibly including the mobile device. The parameters from the database are used to inform the symbolic representation of the different modules so as to result in an individualized representation of each module.

According to an embodiment, the mobile device has an own ID which is accessible for the mobile device's software.

Figure 20:
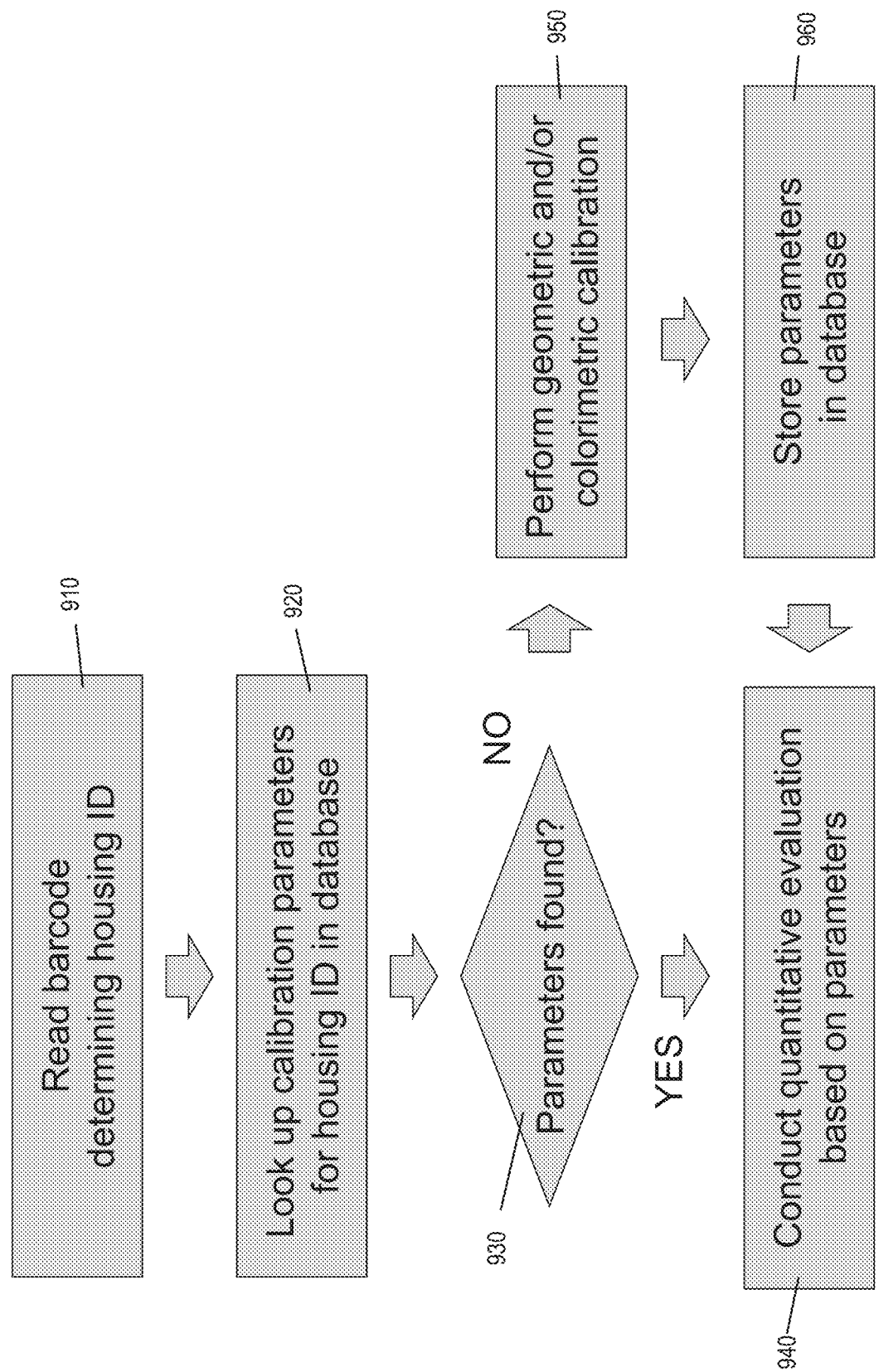
FIG. 20 illustrates a workflow for calibration procedures according to an embodiment.

With respect to FIG. 20 a specific embodiment for a process for adapting a workflow for calibration and/or quantitative evaluation is described.

The camera of the mobile device, the housing 100 and the holder 440 of the light-deflecting element arranged in the housing can have manufacturing variations which result in a slight deviation from the ideal arrangement and alignment of these components. Furthermore, the cartridge holder 710, 810 can also have some tolerances. The tolerances can be evaluated, for example, during assembly of the portable reader module, and stored in the database. Knowledge of the tolerances facilitates a later calibration procedure. For example, when the holder for the light-deflecting element is misaligned, the images captured by the mobile device's camera are shifted relative to an image which would be obtained with a properly aligned light-deflecting element. This may cause a problem for the image analysis algorithm to correctly identify the test zone. The image analysis algorithm needs more time or is even unable to properly recognize the test zone.

When the information on this "misalignment" is available, the image analysis algorithm can use the information to "shift the image back" or to search in a shifted area within the image. This speeds up the analysis and improves the reliability of the calibration.

The information is stored in the database and can be accessed by the mobile device's software.

The process starts at 910 with reading the identification mark such as a barcode and determination of the respective ID, such as the housing ID or the cartridge interface ID. For geometric calibration the unique geometric features of the housing 100, which are defined by the actually used components (housing, cartridge interface, holder for the light-deflecting element), are identified by an algorithm during a calibration procedure. The information on the geometric features is either stored in the database in advance or is obtained during the calibration procedure, for example by recognizing the four corner marks 601 in FIG. 12. These marks can be designed as crosses (see FIG. 11) or alternatively as two or three nested circular elements (similar to a dart board). Alternately, the four corners of the opening 711, 811 of the cartridge interface 710, 810 can be used as well. For later use, the calibration parameters are stored in a database within the mobile device or in an external database. The calibration parameters are accessible through use of the recognized IDs.

During routine operation the software of the mobile device identifies all components via the identification marks such as barcodes, and optionally also itself by its own identification string, checks at 920 if calibration parameters are available for this given combination of hardware components (housing, cartridge interface, holder for light-deflecting element, mobile device) and proceeds, depending on the availability of the calibration parameters at 930, either by performing a calibration procedure or by requesting the calibration parameters and continuing the quantitative evaluation procedure with the obtained calibration parameters.

The software on the mobile device may also checks if a given combination of components is suitable and can accordingly notify the user of an uncontrolled or non-admissible combination.

If calibration parameters for the given combination of hardware components are available in the database, the mobile device proceeds to 940 where the calibration parameters are used to parameterize the quantitative evaluation procedure. Parameterization of the quantitative evaluation procedure includes usage of the retrieved calibration parameters to restrict the area within the captured image to locate the test zone. The image analysis algorithm is thus provided with a specific input in which area of the captured image the test zone is likely to be located. This improves the evaluation process.

If calibration parameters are not available for the given combination of hardware components, a calibration is carried out at 950 as already described further above in detail. The thus obtained calibration parameters are then stored in the database at 960 for later use.

In an implementation for the calibration procedure, the positions of the given features such as the calibration marks as given in FIG. 12 or the four corners of the cartridge interface, are employed to parameterize a geometric transformation, for example a perspective transformation, of an image region, which can be, for example, defined by the four corners, to a normalized image with pre-defined size such as a rectangle.

In an alternative implementation, instead of using an internal database of the mobile device the calibration parameters are stored in a central database. All processes described above can be carried out when using an external or central database. In this case, the mobile device establishes a network connection to a server to obtain access to the database. This access can be additionally controlled by using the ID of the mobile device alone or in combination with the ID of the components.

In the following, an overview is given of an example for a workflow performed for geometric and colorimetric calibration and for quantitative evaluation of tests.

Workflow for Geometric and Colorimetric Calibration

The workflow includes the following initial state:

Setpoints for geometric and colorimetric calibration are stored in the database of mobile device or in an external database.

General processing parameters are stored in database of mobile device or in an external database.

The mobile device is positioned in the first receptacle of the portable reader module.

A calibration cartridge is properly inserted into the second receptacle either directly or through the cartridge adapter.

Step 01: Image acquisition.

Step 02: Robust algorithmic identification of unique features for geometric calibration in image possibly employing general processing parameters.

Step 03: Determination of geometric image calibration employing feature-derived information and target parameters, for example standard dimensions.

Step 04: Application of geometric image calibration, for example perspective transformation, to the acquired image.

Step 05: Algorithmic identification of features for colorimetric calibration in designated calibration areas as described above.

Step 06: Persistent storage of information for geometric and colorimetric calibration in database of mobile device.

Workflow for Quantitative Evaluation Procedure

The workflow includes the following initial state:

Mobile device is calibrated.

Setpoints and control parameters for geometric and colorimetric calibration are stored in the database.

The mobile device is positioned in first receptacle.

A cartridge, which encompasses one or more tests, is properly inserted into the second receptacle either directly or through the cartridge adapter.

Step 01: Select a test type manually from user menu (alternative procedure see step 04).

Step 02: Enter sample ID. This may be done manually or by scanning a sample related barcode provided e.g. on a document accompanying the sample which is subject to the quantitative evaluation procedure. To achieve barcode scanning: first remove cartridge and holder to open up the window in the second receptacle, then evaluate the barcode e.g. by taking an image with the camera (imager) of the mobile device. This may require positioning the housing on the document with the barcode, so that the barcode is visible through the window in the second receptacle via the light deflecting optical element to the camera (imager) of the mobile device. The barcode is than evaluated automatically by the software. After scanning and evaluating the barcode, the cartridge and holder are re-positioned in the housing as required.

Step 03: Image acquisition by the camera (imager) of the mobile device.

Step 04 (alternative to step 01): Identification of test type from barcode on cartridge.

Step 05 (optional): Evaluation of one or more pre-defined barcode regions on housing and cartridge, specifying housing ID and cartridge ID.

Step 06 (optional): Verification of calibration status for given housing ID (if fail: calibration requested, see above workflow for calibration, else: continue workflow).

Step 07: Loading of parameters for further processing from database on mobile device employing test-type ID and (potentially) housing ID.

Step 08: Identification of unique positioning markers in image by template matching employing parameters for geometric calibration.

Step 09: Transformation of image to standard dimensions employing positioning markers and parameters for geometric calibration.

Step 10: Identification of reference elements for colorimetric calibration.

Step 11: Quantitative evaluation of features for colorimetric calibration making use of evaluation parameters.

Step 12: Algorithmic identification of all test result regions based on evaluation parameters specific for test type.

Step 13: Quantitative evaluation of the test result regions (for all tests) employing information from colorimetric calibration features and calibration parameters.

Step 14: Determination of test result (e.g. positive/negative/invalid) using test type specific algorithms and parameters (e.g. thresholds) employing an appropriately parameterized logical function.

Step 15: Persistent storage of corrected quantification values and test results in database (for all tests) on mobile device.

According to an embodiment, a portable reader includes a portable reader module, and a portable device received in the first receptacle of the housing, wherein the portable device includes an imager, a central processing unit, a display, and a light source. The portable device is configured to capture an image of a cartridge including at least one test zone when received in the second receptacle of the housing, to process the captured image, and to display a test result.

According to an embodiment, a method for quantitative analysis of an assay includes providing a portable reader module; placing a portable device having an imager, a central processing unit, a display unit, and a light source in the first receptacle of the portable reader module; placing a cartridge having at least one test zone with at least one test result region in the second receptacle of the portable reader module; capturing an image of the cartridge including the test zone by the imager of the portable device using the light source of the portable device to illuminate the cartridge; analysing the captured image by the portable device to obtain a test result; and displaying the test result in the display unit of the portable device.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

The invention claimed is:

1. A portable reader, comprising:
a portable reader module comprising:
a housing comprising an internal space, a first receptacle configured to removably receive a portable device comprising a lens, an imager, a central processing unit, and a display, the first receptacle comprising a first optical entrance for the imager to the internal space of the housing, and a second receptacle configured to removably receive a cartridge including at least one test zone, the second receptacle comprising a second optical entrance to the internal space of the housing so that the cartridge is visible to and from the internal space;

a first optical reference element comprising at least one of a positional reference, intensity references and colour references, and configured to allow at least one of calibration and self-testing of the portable device, wherein the first optical reference element is arranged inside of the second receptacle separate to the cartridge or in the housing separate to the cartridge;

a light-deflecting optical element arranged within the internal space of the housing to define an optical path between the first optical entrance and the second optical entrance; and an illuminating path for illuminating the cartridge defined in the housing;

wherein the housing is configured to allow the internal space to be light-shielded, wherein the portable device can be received in the first receptacle of the housing, and wherein the portable device is operable to capture an image of the cartridge including the at least one test zone and of the first optical reference element when the cartridge is received in the second receptacle of the housing, to process the captured image, and to display a test result.

2. The portable reader according to claim 1, wherein the second optical entrance is in a field of view of the imager.

3. The portable reader according to claim 1, further comprising an adapter for holding the cartridge, wherein the adapter for holding the cartridge comprises a cartridge interface which is inserted into the second receptacle, and a cartridge holder for holding the cartridge, wherein the cartridge holder cooperates with the cartridge interface when the cartridge holder is releasably attached to the cartridge interface.

4. The portable reader according to claim 3, wherein one of the cartridge holder and cartridge interface comprises magnetic bodies and the other one of the cartridge holder and the cartridge interface comprises metal pins or discs which cooperate together with the magnetic bodies to hold the cartridge holder in place relative to the cartridge interface.

5. The portable reader according to claim 1, further comprising one or more identification marks uniquely identifying at least one individual component or part of the portable reader module.

6. The portable reader according to claim 1, wherein the portable device comprises a light source, and wherein the illuminating path comprises a reflector for reflecting light from the light source to the cartridge.

7. The portable reader according to claim 1, further comprising a second optical reference element configured to allow at least one of calibration and self-testing of the portable device, the second optical reference element being differing from the first optical reference element in at least one of pattern, greyscale, and colour.

8. The portable reader according to claim 1, wherein the second receptacle is configured to be placeable, with our without an inserted cartridge, onto a surface so that the portable device is in a substantially upright position relative to the surface.

9. The portable reader module according to claim 1, wherein at least one of the first receptacle and the second receptacle comprises holders for retaining the portable device in the first receptacle and the cartridge in the second receptacle.

10. The portable reader according to claim 1, further comprising an adjustment element arranged in the housing, the adjustment element being configured to adjust at least one of the location and orientation of the light-deflecting optical element.

11. The portable reader according to claim 1, wherein the first receptacle comprises a bottom element which is removably attached to the housing and which comprises a holder to hold the light-deflecting optical element in the internal space.

12. The portable reader according to claim 1, wherein at least portions of the internal space are provided with a low-reflection surface.

13. The portable reader according to claim 1, wherein the light-deflecting optical element comprises a mirror or a prism.

14. The portable reader according to claim 1, wherein the housing further comprises an opening which allows access to the internal space, and wherein the first receptacle comprises a bottom element which is removably attached to the housing, which closes the opening and which comprises a holder to hold the light-deflecting optical element in the internal space.

15. The portable reader module according to claim 1, wherein the positional reference comprises at least one of crosses, lines, and checker boards, wherein the intensity references comprises at least one of grey scales, grey step wedges, checker broads, line pattern and noise pattern, and/or wherein the colour references comprises at least one of colour scales, colour step wedges, gratings and a prism.

16. The portable reader module according to claim 3, wherein the cartridge holder comprises at least one of an open cavity for accommodating the cartridge aligned with respect to the cartridge holder and adjusting elements provided in the cavity and engaging with the cartridge when placed into the cartridge holder.

17. The portable reader module according to claim 14, wherein the holder is formed like a housing over the first optical entrance for shielding the light-deflecting optical element and the first optical entrance from light emanating from the light source.

18. Using of a portable reader, comprising:
a portable reader module comprising
a housing comprising an internal space, a first optical reference element comprising at least one of a positional reference, intensity references and color references, a first receptacle configured to removably receive a portable device comprising an imager, the first receptacle comprising a first optical entrance for the imager to the internal space of the housing, and a second receptacle configured to removably receive a cartridge, the second receptacle comprising a second optical entrance to the internal space of the housing so that the cartridge is visible to and from the internal space, wherein the first optical reference element is arranged inside of the second receptacle separate to the cartridge or in the housing separate to the cartridge;
a light-deflecting optical element arranged within the internal space of the housing to define an optical path between the first optical entrance and the second optical entrance; and
an illuminating path for illuminating the cartridge defined in the housing;
wherein the housing is configured to allow the internal space to be light-shielded; and a portable device received in the first receptacle of the housing, the portable device comprising an imager, a processing unit, and a display, for capturing with the imager an image of a cartridge including at least one test zone and of the first optical reference element when the cartridge is received in the second receptacle of the housing, for processing the captured image with the processing unit, and for displaying a test result on the display.

\* \* \* \* \*